(12) United States Patent
West

(10) Patent No.: US 10,047,340 B2
(45) Date of Patent: Aug. 14, 2018

(54) BANK OF STEM CELLS FOR PRODUCING CELLS FOR TRANSPLANTATION HAVING HLA ANTIGENS MATCHING THOSE OF TRANSPLANT RECIPIENTS, AND METHODS FOR MAKING AND USING SUCH A STEM CELL BANK

(71) Applicant: ADVANCED CELL TECHNOLOGY, INC., Marlborough, MA (US)

(72) Inventor: Michael West, Southborough, MA (US)

(73) Assignee: Advanced Cell Technology, Inc., Worcester, MA (US)

( * ) Notice: Subject to any disclaimer, the term of this patent is extended or adjusted under 35 U.S.C. 154(b) by 0 days.

(21) Appl. No.: 13/721,618

(22) Filed: Dec. 20, 2012

(65) Prior Publication Data

US 2013/0276154 A1 Oct. 17, 2013

Related U.S. Application Data

(63) Continuation of application No. 10/445,195, filed on May 27, 2003, now abandoned.

(60) Provisional application No. 60/382,616, filed on May 24, 2002, provisional application No. 60/448,585, filed on Feb. 21, 2003.

(51) Int. Cl.
*C12N 5/00* (2006.01)
*C12N 5/0735* (2010.01)
*C12N 15/85* (2006.01)
*A61K 35/12* (2015.01)

(52) U.S. Cl.
CPC ........... *C12N 5/0606* (2013.01); *C12N 15/85* (2013.01); *A01K 2217/05* (2013.01); *A01K 2267/0393* (2013.01); *A61K 35/12* (2013.01); *C12N 2510/00* (2013.01); *C12N 2517/10* (2013.01)

(58) Field of Classification Search
CPC ... C12N 5/0606; C12N 15/85; C12N 2517/10
See application file for complete search history.

(56) References Cited

U.S. PATENT DOCUMENTS

| | | | |
|---|---|---|---|
| 5,004,681 A | 4/1991 | Boyse et al. | |
| 5,087,570 A | 2/1992 | Weissman et al. | |
| 5,192,533 A | 3/1993 | Elliott et al. | |
| 5,416,260 A * | 5/1995 | Koller et al. | 800/11 |
| 5,639,618 A | 6/1997 | Gay | |
| 5,733,727 A | 3/1998 | Field | |
| 5,851,832 A | 12/1998 | Baetge et al. | |
| 5,922,601 A | 7/1999 | Baetscher et al. | |
| 5,942,225 A | 8/1999 | Bruder et al. | |
| 5,945,577 A | 8/1999 | Stice et al. | |
| 5,993,387 A | 11/1999 | Moore et al. | |
| 6,080,576 A | 6/2000 | Friedrich et al. | |
| 6,123,727 A | 9/2000 | Cao et al. | |
| 6,136,566 A | 10/2000 | Bradley et al. | |
| 6,197,575 B1 | 3/2001 | Griffith et al. | |
| 6,207,371 B1 | 3/2001 | Zambrowicz et al. | |
| 6,214,369 B1 | 4/2001 | Grande et al. | |
| 6,215,041 B1 * | 4/2001 | Stice | A01K 67/02 435/325 |
| 6,280,718 B1 | 8/2001 | Kaufman et al. | |
| 7,030,292 B2 * | 4/2006 | Yan et al. | 800/24 |
| 2002/0127715 A1 * | 9/2002 | Benvenisty et al. | 435/366 |
| 2002/0155601 A1 | 10/2002 | Yan et al. | |
| 2006/0083722 A1 | 4/2006 | Cibelli et al. | |

FOREIGN PATENT DOCUMENTS

| | | |
|---|---|---|
| EP | A-1 293 661 | 3/2003 |
| JP | 2000217576 | 8/2000 |
| WO | WO-A-99/50426 | 7/1999 |
| WO | WO 01/30978 A1 | 5/2001 |
| WO | WO 01/32015 | 5/2001 |
| WO | WO 2002/057429 A2 | 7/2002 |
| WO | WO 02/102997 A | 12/2002 |
| WO | WO 03/046141 A2 | 6/2003 |

OTHER PUBLICATIONS

American Red Cross, printout from www.redcrossbloos.org/learn-about-blood/blood-types, printed Dec. 5, 2013, pp. 1-2.*
Westhusin et al. Theriogenology 55:35-49, 2001.*
Cibelli et al. J Reneg Med 2:25-32, 2001.*
Davis. J Anim Sci 85(13 suppl):E32-5, 2007.*
Stem Cells: Scientific Progress and Future Directions. Chapter 1: the Stem Cell, p. 1, 2001.*
Hua et al, Anim Reprod Sci, Mar. 6, 2007[Epub ahead of print], pp. 1-13 printout.*
Labosky et al., "Mouse Embryonic Germ (EG) Cell Lines: Transmission Through the Germline and Differences in the Methylation Imprint of Insulin-Like Growth Factor 2 Receptor (Igf2r) Gene Compared with Embryonic Stem (ES) Cell Lines," *Development* 120:3197-3204 (1994).
Lanza et al., "Human Therapeutic Cloning," *Nature Medicine* 5(9):975-977 (1999).
Lee et al., "Efficient Generation of Midbrain and Hindbrain Neurons from Mouse Embryonic Stem Cells," *Nature Biotechnology* 18:675-679 (2000).
Lillien et al., "BMP and FGF Regulate the Development of EGF-Responsive Neural Progenitor Cells," *Development* 127:4993-5005 (2000).
Martin, "Isolation of a Pluripotent Cell Line from Early Mouse Embryos Cultured in Medium Conditioned by Teratocarcinoma Stem Cells," *Proc. Natl. Acad. Sci. USA* 78(12):7634-7638 (1981).

(Continued)

*Primary Examiner* — Marcia S Noble
(74) *Attorney, Agent, or Firm* — DLA Piper LLP (US)

(57) ABSTRACT

Methods for producing stem cell banks, preferably human, which optionally may be transgenic, e.g., comprised of homozygous MHC allele cell lines are provided. These cells are produced preferably from parthenogenic, IVF, or same-species or cross-species nuclear transfer embryos or by dedifferentiation of somatic cells by cytoplasm transfer. Methods for using these stem cell banks for producing stem and differentiated cells for therapy, especially acute therapies, and for screening for drugs for disease treatment are also provided.

18 Claims, 12 Drawing Sheets

(56) References Cited

OTHER PUBLICATIONS

Matsuda et al., "Glypican-1 is Overexpressed in Human Breast Cancer and Modulates the Mitogenic Effect of Multiple Heparin-Binding Growth Factors in Breast Cancer Cells," Cancer Research 61:5562-5569 (2001).
Matsui et al., "Derivation of Pluripotential Embryonic Stem Cells from Murine Primordial Germ Cells in Culture," Cell 70:841-847 (1992).
Murray et al., "The Genes for Leukemia Inhibitory Factor and Interleukin-6 Are Expressed in Mouse Blastocyst Prior to the Onset of Hemopoiesis," Molecula and Cellular Biology 10(9):4953-4956 (1990).
Nichols et al., "Derivation of Germline Competent Embryonic Stem Cells with a Combination of Interleukin-6 and Soluable Interleukin-6 Receptor," Experimental Cell Research 215:237-237 (1994).
ODorico et al., "Multilineage Differentiation from Human Embryonic Stem Cell Lines," Stem Cells 19:193-204 (2001).
Ogawa et al., "Expression of a-Integrin Defines the Earliest Precursor of Hematopoietic Cell Lineage Diverged From Endothelial Cells," Blood 93(4):1168-1177 (1999).
Paquin et al., "Oxytocin Induces Differentiation of P19 Embryonic Stemm Cells to Cardiomyocytes," PNAS 99(14):9550-9555 (2002).
Resnick et al., "Long-Term Proliferation of Mouse Primordial Germ Cells in Culture," Nature 359:550-551 (1992).
Reubinoff et al., "Embryonic Stemm Cell Lines from Human Blastocysts: Somantic Differentiation In Vitro," Nature Biotechnology 18:399-404 (2000).
Reubinoff et al., "Neural Progenitors from Human Embryonic Stem Cells," Nature Biotechnology 19:1134-1140 (2001).
Rohwedel et al., "Loss of 131 Integrin Function Results in a Retardation of Myogenic, But an Acceleration of Neuronal, Differentiation of Embryonic Stem Cells in Vitro," Development Biology 201:167-184 (1998).
Rohwedel et al., "Muscle Cell Differentiation of Embryonic Stem Cells Reflects Myogenesis In Vivo: Developmentally Regulated Expression of Myogenic Determination Genes and Functional Expression of Ionic Currents," Developmental Biology 164:87-101 (1994).
Russ et al., "Identification of Genes Induced by Factor Deprivation in Hematopoietic Cells Undergoing Apoptosis Using Gene-Trap Mutagenesis and Site-Specific Recombination," Proc. Nat. Acad. Sci. USA 93:15279-15284 (1996).
Sakamoto et al., "Combined Evaluation of NGF and P75NgFR Expression is a Biomarker for Predicting Prognosis in Human Invasive Ductal Breast Carcinoma," Oncology Report 8:973980 (2001).
Salminen et al., "Effcient Poly A Trap Approach Allows the capture of Genes Specifically Active in Differentiated Embryonic Stem Cells and In Mouse Embryos," Developmental Dynamics 212:326-333 (1998).
Schuldiner et al., "Effects of Eight Growth Factors on the Differentiation of Cells Derived from Human Embryonic Stem Cells," PNAS 97(21):11307-11312 (2000).
Shamblott et al., "Derivation of Pluripotent Stem Cells from Cultured Human Primordial Germ Cells," Proc. Natl. Acad. Sci. USA 95:13726-13731 (1998).
Shen et al., "Leukemia Inhibitory Factor is Expressed by the Preimplantation Uterus and Selectively Blocks Primitive Ectoderm Formation In Vitro," Proc. Natl. Acad. Sci. USA 89:8240-8244 (1992).
Biesecker et al., "Interleukin-6 is a Component of Human Umbilical Cord Serum and Stimulates Hematopoiesis in Embryonic Stme Cells In Vitro," Experimental Hematology 21:774-778 (1993).
Bonaldo et al., "Efficient Gene Trap Screening for Novel Developmental Genes Using IRESpgeo Vector and In Vitro Preselection," Experimental Cell Research 244:125-136 (1998).
Brannen et al., "In Vitro Differentiation of Multipotent Human Neural Progenitors in Serum-Free Medium," NeuroReport 11(5):1123-1128 (2000).

Buttery et al., "Differentiation of Osteoblasts and In Vitro Bone Formation from Murine Embryonic Stem Cells," Tissue Engineering 7(1):89-99 (2001).
Cecconi et al., "Gene Trap: A Way to Identify Novel Genes and Unravel Their Biological Function," FEBS Letters 480:63-71 (2000).
Chowdhury et al., "Evidence for the Stochastic Integration of Gene Trap Vectors into Mouse Germline," Nucleic Acids Research 25(8):1532-1536 (1997).
Cibelli et al., "Parthenogenetic Stem Cells in Nonhuman Primates," Science 295:819 (2002).
Couldrey et al., "Disruption of Murine a-Enolase by a Retroviral Gene Trap Results in Early Embryonic Lethality," Developmental Dynamics 212:284-292 (1998).
Dunn et al., "A Knock-Out Model of Paroxysmal Nocturnal Hemoglobinuria: Pig-a Hematopoiesis is Reconstituted Following Intercellular Transfer of GPI-Anchored Proteins," Proc. Natl. Acad. Sci. USA 93:7938-7943 (1996).
Durick et al., "Hunting with Traps: Genome-Wide Strategies for Gene Discovery and Fnctional Analysis," Genome Research 9:1019-1025 (1999).
Dymecki et al., "Using FLP-Recombinase to Characterize Expansion of WNT1-Expressing Neural Progenitors in the Mouse," Developmental Biology 201:57-65 (1998).
Eckert et al., "A Colorimetric Immunoassay for the Detection of E-Cadherin and Carcinoembryonic Antigen (CEA) Expression on Human Colon Carcinoma Cell Lines In Vitro," Cancer Letters 105:1-4 (1996).
Era et al., "Characterization of Hematopoietic Lineage-Specific Gene Expression by ES Cell In Vitro Differentiation Induction System," Blood 95(3):870-878 (2000).
Evans et al., "Establishment in Culture of Pluripotential Cells from Mouse Embryos," Nature 292:154-156 (1981).
Forrester et al., "An Induction Gene Trap Screen in Embryonic Stem Cells: Identification of Genes That Respond to Rerinoic Acid In Vitro," Proc. Natl. Acad. Sci. USA 93:1677-1682 (1996).
Gmyrek et al., "Normal and Malignant Prostate Epithelial Cells Differ In Their Response to Hepatocyte Growth Factor/Scatter Factor," American Journal of Pathology 159(2):579-590 (2001).
Gossler et al., "Mouse Embryonic Stem Cells and Reporter Constructs to Detect Developmentally Regulated Genes," Science 244:463-465 (1989).
Grabel et al., "Using EC and ES Cell Culture to Study Early Development: Recent Observations on Indian Hedgehog and Bmps," Int. J. Dev. Biol. 42:917-925 (1998).
Hariry et al., "FGF-1 and FGF-2 Modulate the E-Cadherin/Catenin System in Pancreatic Adenocarcinoma Cell Lines," British Journal of Cancer 84(12):1656-1663 (2001).
Henkel et al., "PU.1 But Not ETS-2 is Essential for MAcrophage Development From Embryonic Stem Cells," Blood 88(8):2917-2926 (1996).
Hicks et al., "Functional Genomics in Mice by Tagged Sequence Mutagenesis." Nature Genetics 16:338-344 (1997).
Hirashima et al., "Maturation of Embryonic Stem Cells Into Endothelial Cells in An In Vitro Model of Vasculogenesis," Blood 93(4):1253-1263 (1999).
Kawasaki et al., "Generation of Dopaminergic Neurons and Pigmented Epithelia From Primate ES Cells ny Stromal Cell-Derived Inducing Activity," PNAS 99(3):1580-1585 (2002).
Kelly et al., "DNA Microarray Analyses of Genes Regulated During the Differentiation of Embryonic Stem Cells," Molecular Reproduction and Development 56:113-123 (2000).
Matsuda et al., "Glypican-1 Overexpressed in Human Breast Cancer and Modulates the Mitogenic Effect of Multiple Heparin-Binding Growth Factors in Breast Cancer Cells," Cancer Research 61:5562-5569 (2001).
Murray et al., "The Genes for Leukemia Inhibitory Factor and Interleukin-6 Are Expressed in Mouse Blastocyst Prior to the Onset of Hemopoiesis," Molecular and Cellular Biology 10(9):4953-4956 (1990).
Nichols et al., "Derivation of Germline Competent Embryonic Stem Cells with a Combination of Interleukin-6 and Soluble Interleukin-6 Receptor," Experimental Cell Research 215:237-239 (1994).

(56) References Cited

OTHER PUBLICATIONS

Paquin et al., "Oxytocin Induces Differentiation of P19 Embryonic Stem Cells to Cardiomyocytes," *PNAS* 99(14):9550-9555 (2002).

Reubinoff et al., "Embryonic Stem Cell Lines from Human Blastocysts: Somatic Differentiation In Vitro," *Nature Biotechnology* 18:399-404 (2000).

Sakamoto et al., "Combined Evalutation of NGF and P75NGFR Expression is a Biomarker for Predicting Prognosis in Human Invasive Ductal Breast Carcinoma," *Oncology Report* 8:973980 (2001).

Salminen et al., "Efficient Poly A Trap Approach Allows the Capture of Genes Specifically Active in Differentiated Embryonic Stem Cells and In Mouse Embryos," *Developmental Dynamics* 212:326-333 (1998).

Skarnes et al., "A Gene Trap Approach in Mouse Embryonic Stem Cells: The LacZ Reporter is Activated by Splicing, Reflects Endogenous Gene Expression, and is Mutagenic in Mice," *Genes & Development* 6:903-918 (1992).

Slager et al., "Transforming Growth Factor-I3 in the Early Mouse Embryo: Implications for the Regulation of Muscle Formation and Implantation," *Developmental Genetics* 14:212-224 (1993).

Stanford et al., "Expression Trapping: Identification of Novel Genes Expressed in Hematopoietic and Endothelial Lineages By Gene Trappin in ES Cells," *Blood* 92:(12):46224631 (1998).

Suzuki et al., "Preferential Differentiationof P19 Mouse Embryonal Carcinoma Cells Into Smooth Muscle Cells," *Circ. Res.* 78:395-404 (1996).

Thomson et al., "Isolation of a Primate Embryonic Stem Cell Line," *Proc. Natl. Acad. Sci. USA* 92:7844-7848 (1995).

Thomson et al., "Neural Differentiation of Rhesus Embryonic Stem Cells," *APMIS* 106:149-157 (1998).

Thorey et al., "Selective Disruption of Genes Transiently Induced in Differentiating Mouse Embryonic Stem Cells by Using Gene Trap Mutagenesis and Site-Specific Recombination," *Molecular and Cellular Biology* 18(5):3081-3088 (1998).

Timeus et al., "FLT-3 and Its Ligand Are Expressed in Neural Crest-Derived Tumors and Promote Survival and Prolifereation of Their Cell Lines," *Laboratory Investigation* 81(7):10251037 (2001).

Townley et al., "Rapid Sequence Analysis of Gene Trap Integrations to Generate A Resource of Insertional Mutations in Mice," *Genome Research* 7:293-298 (1997).

Vittet et al., "Embryonic Stem Cells Differentiate In Vitro to Endothelial Cells Through Successive Maturation Steps," *Blood* 88(9):3424-3431 (1996).

Voss et al., "Efficiency Assessment of the Gene Trap Approach," *Developmental Dynamics* 212:171-180 (1998).

Wiles et al., "Embryonic Stem Cells Development in a Chemically Defined Medium," *Experimental Cell Research* 247:241-248 (1999).

Wiles et al., "Establishment of a Gene-Trap Sequence Tag Library to Generate Mutant Mice from Embryonic Stem Cells," *Nature Genetics* 24:13-14 (2000).

Wiles et al., "Multiple Hematopoietic Lineages Develop from Embryonic Stem (ES) Cells in culture," *Development* 111:259-267 (1991).

Wirl et al., "Mammary Epithelial Cell Differentiation In Vitro is Regulated by an Interplay of EGF Action and Tenascin-C Downregulation," *Journal of Cell Science* 108:2445-2456 (1995).

Yiu et al., "SPARC (Secreted Protein Acidic and Rich in Cysteine) Induces Apoptosis in Ovarian Cancer," *American Journal of Pathology* 159:(2):609-622 (2001).

Yuen et al., "Generation of a Primitive Erythroid Cell Line and Promotion of Its Growth by Basic Fibroblast Growth Factor," *Blood* 91(9):3202-3209 (1998).

Zambrowicz et al., "Comprehensive Mammalian Genetics: History and Future Prospects of Gene Trapping in the Mouse," *Int. J. Dev. Biol.* 42:1025-1036 (1998).

Zambrowicz et al., "Disruption and Sequence Identification 2,000 Genes in Mouse Embryonic Stem Cells," *Nature* 392:608-611 (1998).

Zhang et al., "In Vitro Differentiation of Transplantable Neural Precursors from Human Embryonic Stem Cells," *Nature Biotechnology* 19:1129-1133 (2001).

Zhang et al., "Vasculogenesis from Embryonic Bodies of Murine Embryonic Stem Cells Transfected by Tgf-131 Gene," *Endothelium* 602:95-106 (1998).

Zinyk et al., "Fate Mapping of the Mouse Midbrain-Hindbrain Construction Using a Site-Specific Recombination System," *Current Biology* 8(11):865-868 (1998).

Birmingham (2003), "The move to preserve therapeutic cloning," J Clin Invest, 112(11): 1600-1601.

Boquest et al. (May 1, 2002), "Production of cloned pigs from cultured fetal fibroblast cells," Biol Reprod, 66(5):1283-7.

Byrne et al. (2007), "Producing primate embryonic stem cells by somatic cell nuclear transfer," Nature, 450(7169):497-502.

Cibelli et al. (1998), "Teansgenic bovine chimeric offspring produced from somatic cell-derived stem-like cells," Nat. Biotech., 16(7):642-6.

French et al. (2008), "Developmentof human cloned blastocysts following somatic cell nuclear transfer with adult fibroblasts," Stem Cells,26(2):485-93.

Lanza et al. (2003), "Comment on Molecular Correlates of Primate Nuclear Transfer Failures," Science, 301, 1482b.

Lanza et al. (2001), Cloned cattle can be healthy and normal, Science, 294(5548):1893-4.

Liu et al. (Feb. 2000), "A reliable, noninvasive technique for spindle imaging and enucleation of mammalian oocytes," Nature Biotechnology, 18(2):223-5.

Mitalipov et al. (2007), "Reprogramming following somatic cell nuclear transfer in primates is dependent upon nuclear remodeling," Hum Reprod. 22(8):2232-42.

Mitalipov et al. (Apr. 1999), "Development of nuclear transfer and parthenogenetic rabbit embryos activated with inositol 1,4,5-trisphosphate," Biol Reprod, 60(4):821-7.

Munsie et al. (2000), "Isolation of pluripotent embryonic stem cells from reprogrammed adult mouse somatic cell nuclei," Curr. Bio., 10 :989-992.

Pickrell (2003), "Chimps Belong on Human Branch of Family Tree, Study Says," National Geographic News.

Schatten et al. (2003), Response to Comment on "Molecular Correlated of Primate Nuclear Transfer Failures," Science 301, 1482.

Simerly et al. (2004), "Embryogenesis and blastocyst development after somatic cell nuclear transfer in nonhuman primates: overcoming defects caused by meiotic spindle extraction," Dev Biol. Dec. 15, 2004,276(2):237-52.

Stojkovic et al. (2005), "Derivation of a human blastocyst after heterologous nuclear transfer to donated oocytes," PBM Online, 11(2):226-231.

Wakayama et al. (1998), "Full-term development of mice from enucleated oocytes injected with cumulus cell nuclei," Nature, 394(6691):369-74.

Wilting and Taylor (2007), "Primates Join the Club," Nature 450(7169):485-486.

Mitalipov, S. M. et al:: *"Parthenogenetic Activation of Rhesus Monkey Oocytes and Reconstructed Embryos"* Academ. Press, US, vol. 65, No. 1, Jul. 1, 2001; pp. 253-259, XP001117868, ISSN: 0006-3363, DOI: 10.1095/BIOLREPROD65.1.253.

Van Doorninck, J. H. et al:: *"A Mouse Model for the Cystic Fibrosis Delta-F508"*, EMBO Journal, Oxford University Press, Surrey, GB, vol. 14, No. 18, Jan. 1, 1995, pp. 4403-4411, XP008069832, ISSN: 0261-4189.

Kim, Kitai et al. *"Histocompatible embryonic stem cells by parthenogenesis"*, Science, American Association for the Advancement of Science, Washington, DC; US, vol. 315, No. 5811, Jan. 26, 2007, pp. 482-486, XP002467552, ISSN: 0036-8075, DOI: 10.1126/SCIENCE.1133542.

European Search Report Regarding EP 13 18 6524.

Cibelli, Jose B. et al: *"Embryonic stem cells from parthenotes"*; Methods in Enzymology, Academic Press, US, vol. 418, Jan. 1, 2006, pp. 117-135.

(56) References Cited

OTHER PUBLICATIONS

Lin, H et al:: "*Multilineage Potential of Homozygous Stem Cells Derived From Metaphase II Oocytes*"; Stem Cells, Alphamed Press, Dayton, OH, US, vol. 21, No. 2, Jan. 1, 2003, pp. 152-161.
European Examination Report dated Jul. 30, 2015, regarding EP 03 736 723.2.
Examination Report regarding CA 2,505,598.

* cited by examiner

BANK OF STEM CELLS FOR PRODUCING CELLS FOR TRANSPLANTATION HAVING HLA ANTIGENS MATCHING THOSE OF TRANSPLANT RECIPIENTS, AND METHODS FOR MAKING AND USING SUCH A STEM CELL BANK

CROSS-REFERENCE TO RELATED APPLICATIONS

This application is a continuation of U.S. application Ser. No. 10/445,195, filed May 27, 2003, which claims the benefit of U.S. Provisional Application No. 60/382,616 filed May 24, 2002, and U.S. Provisional Ser. No. 60/448,585, filed on Feb. 21, 2003, each of which is hereby incorporated by reference in their entirety.

FIELD OF THE INVENTION

The invention described herein relates to methods for producing a collection of human and non-human stem cell cultures, preferably human stem cell cultures, each of which contains totipotent or pluripotent stem cells that have genes encoding the same set of critical cell surface antigenic proteins, e.g., histocompatibility antigens (e.g., HLA antigens in the case of human) as are present on the cells of members of a human population. (By critical antigens is meant the set of antigens that form the major histocompatibility complex and other antigens such as blood group antigens that are involved in immuno-mediated rejection when collogenic cells and tissues are transplanted into donors that express a different set of histocompatibility and other critical antigens). The methods disclosed herein include deriving such human stem cell cultures from cells of early embryos produced e.g. by in vitro fertilization, parthenogenesis, and by nuclear transfer. Also, stem cells can be produced by transfer of cytoplasm from embryonic cells, e.g. oocytes, early embryonic cells or ES cells into somatic cells.

The invention described herein also relates to methods wherein such human and non-human stem cell cultures are induced to differentiate ex or in vivo into cell types that are useful for therapeutic cell transplantation; and to methods by which the differentiated cells are isolated from other cell types. The invention also relates to methods in which stem cell-derived differentiated cells having a selected set of critical cell surface antigens are therapeutically transplanted or engrafted to a recipient, e.g., a human patient in need of a cell transplant having cells that express the same critical cell surface antigens. The invention further relates to a collection or "bank" of cultures of different types of stem cells, each culture having a different set of genes encoding cell surface antigenic proteins present in a human population; to compositions comprising the individual stem cell cultures that make up such a stem cell bank; and to compositions comprising differentiated cells derived from such stem cells.

Preferably, stem cell banks produced according to the invention will comprise stem cell lines which are homozygous for MHC alleles which occur very frequently in the human population. Typically, a stem cell bank according to the invention will comprise at least 15 stem cell lines and more preferably at least 100 to 1000 stem cell lines. Thereby, the stem cell bank will provide maximal therapeutic and diagnostic efficacy as it will contain cells that are histocompatible for a wide range of potential transplant recipients.

BACKGROUND OF THE INVENTION

A. Histocompatibility and Transplant Rejection:

Histocompatibility is a largely unsolved problem in transplant medicine. Rejection of transplanted tissue is the result of an adaptive immune response to alloantigens on the grafted tissue by the transplant recipient. The alloantigens are "non-self proteins, i.e., antigenic proteins that vary among individuals in the population and are identified as foreign by the immune system of a transplant recipient. The antigens on the surfaces of transplanted tissue that most strongly evoke rejection are the blood group (ABO) antigens and the major histocompatibity complex (MHC) proteins and in the case of humans, the human leukocyte antigen (HLA) proteins.

The blood group antigens were first described by Landsteiner in 1900; they are branched oligosaccharides that are attached to proteins and lipids on the surfaces of red blood cells, endothelial cells, and other cells, and are also present in secretions such as saliva. Compatibility of the blood group antigens of the ABO system of a vascularized organ or tissue transplant with those of the transplant recipient is generally required; but blood group compatibility may be unnecessary for many types of cell transplants.

The HLA proteins are encoded by clusters of genes that form a region located on chromosome 6 known as the Major Histocompatibility Complex, or MHC, in recognition of the important role of the proteins encoded by the MHC loci in graft rejection. Accordingly, the HLA proteins are also referred to as MHC proteins. The MHC genes and proteins will be used interchangeably in this application as the application encompasses human and non-human animal applications. The HLA or MHC proteins normally play a role in defending the body against foreign pathogens such as viruses, bacteria, and toxins. They are cell surface glycoproteins that bind peptides at intracellular locations and deliver them to the cell surface, where the combined ligand is recognized by a T cell. Class I MHC proteins are found on virtually all of the nucleated cells of the body. The class I MHC proteins bind peptides present in the cytosol and form peptide-MHC protein complexes that are presented at the cell surface, where they are recognized by cytotoxic CD8+ T cells. Class II MHC proteins are usually found only on antigen-presenting cells such as B lymphocytes, macrophages, and dendritic cells. The class II MHC proteins bind peptides present in a cell's vesicular system and form peptide-MHC protein complexes that are presented at the cell surface, where they are recognized by CD4+ T cells. CD4+ T cells activated by class II MHC proteins undergo clonal expansion with production of regulatory cytokines that signal helper and cytotoxic T cells. Unfortunately for those in need of transplants, the frequency of T cells in the body that are specific for non-self MHC molecules is relatively high, with the result that differences at MHC loci are the most potent critical elicitors of rejection of initial grafts. Rejection of most transplanted tissues is triggered predominantly by the recognition of class I MHC proteins as non-self proteins. T cell recognition of foreign antigens on the transplanted tissue sets in motion a chain of signaling and regulatory events that causes the activation and recruitment of additional T cells and other cytotoxic cells, and culminates in the destruction of the transplanted tissue. (Charles A. Janeway et al., *Immunobiology*, Garland Publishing, New York, N.Y., 2001, p. 524).

B. The Genes Encoding MHC Proteins:

The MHC genes are polygenic—each individual possesses multiple, different MHC class I and MHC class II genes. The MHC genes are also polymorphic—many variants of each gene are present in the human and non-human population. In fact, the MHC genes are the most polymorphic genes known. Each MHC Class I receptor consists of a variable α chain and a relatively conserved β2-microglobulin chain. Three different, highly polymorphic class I α chain genes have been identified. These are called HLA-A, HLA-B, and HLA-C. Variations in the α chain chains account for all of the different class I MHC genes in the population. MHC Class II receptors are also made up of two polypeptide chains, an α chain and a β chain, both of which are polymorphic. In humans, there are three pairs of MHC class II α and β chain genes, called HLA-DR. HLA-DP, and HLA-DQ. Frequently, the HLA-DR cluster contains an extra gene encoding a β chain that can combine with the DR α chain; thus, an individual's three MHC Class II genes can give rise to four different MHC Class II molecules.

In humans, the genes encoding the MHC class I α chains and the MHC class II α and β chain are clustered on the short arm of chromosome 6 in a region that extends over from 4 to 7 million base pairs that is called the major histocompatibility complex. Every person usually inherits a copy of each HLA gene from each parent. If an individual's two alleles for a particular MHC locus encode structurally different proteins, the individual is heterozygous for that MHC allele. If an individual has two MHC alleles that encode the same MHC molecule, the individual is homozygous for that MHC allele. Because there are so many different variants of the MHC alleles in the population, most people have heterozygous MHC alleles. The numbers of different alleles found for each type of MHC class I α chain and MHC class II α and β chains as of January 2003 are shown in Table 1.

TABLE 1

The numbers of different alleles for the polymorphic MHC class I and class II chains identified as of January, 2003.

| MHC chain | no. of alleles |
|---|---|
| HLA-A | 266 |
| HLA-B | 511 |
| HLA-C | 6 |
| HLA-DRA | 3 |
| HLA-DRB | 403 |
| HLA-DQA1 | 23 |
| HLA-DQB1 | 53 |
| HLA-DPA1 | 20 |
| HLA-DPB1 | 101 |

The data in Table 1 is from the Internet web site of the Informatics Group of the Anthony Nolan Trust, The Royal Free Hospital, Hampstead, London, England. Lists of identified HLA Class I and Class II alleles are also available at the same web site.

C. Matching MHC Types to Inhibit Rejection of Transplants:

Since the recognition that-non-self-M1-G-molecules are a major determinant of graft rejection, much effort has been put into developing assays to identify the MHC types present on the cells of tissue to be transplanted, and on the cells of transplant recipients, in order to match the types of MHC molecules present in the transplant tissue with those of the recipient. Tissue typing, the detection of MHC antigens, is performed by various means; for example, (i) by serology, using antibodies specific for particular MHC molecules to detect the presence of the targeted MHC molecules on donor or recipient cells, e.g., by the lymphocytotoxicity test; (ii) by detection of antibodies of a transplant recipient that bind specifically to a MHC protein of transplant tissue; and (iii) by direct analysis of the nucleotide sequence of the DNA of the MHC alleles. Most tissue typing for organ banking purposes is done by determining the blood type (ABO typing) and by typing the patient's and donor cells using serological methods; however, the use of rapid and reliable DNA-specific methods is increasing. Such methods can employ sequence-specific oligonucleotide primers and amplification by the polymerase chain reaction (PCR), and can be augmented by combining fluorescent detection methods with the use of a DNA chip to which are bound sequence specific oligonucleotides designed to detect unique sequences present in the different MHC alleles.

At present, tissue typing to match the HLA antigens of a transplant with those of a recipient is usually limited to the Class I HLA-A and -B antigens, and the Class II HLA-DR antigens. Most transplant donors are unrelated to the transplant recipient, and finding a tissue type to match that of the recipient usually involves matching the blood type and as many as possible of the 6 HLA alleles—two for each HLA-A, -B, and -DR locus. Transplant centers do not usually consider potential incompatibilites at other FILA loci, such as HLA-C and HLA-DPB1, although mismatches at these loci can also contribute to rejection. Considering only the combinations of maternal and paternal alleles of the HLA-A. HLA-B, and HLA-DR loci identified to date, there is a complexity of billions of possible tissue types. The task of matching HLA types of organs for transplant is simplified in that HLA-A and HLA-B are usually identified serologically. The number of HLA antigens identified serologically is considerably less than the number of different MLA antigens based on DNA sequencing. The World Health Organization (WHO) has recognized 28 distinct antigens in the HLA-A locus and 59 in the HLA-B locus, based on serological typing. Matching organs is also simplified to some extent by the fact that some alleles are much more common than others. Some of the more common HLA-A and HLA-B alleles are shown in Table 2:

TABLE 2

Frequency of common HLA-A and HLA-B alleles in the population.

| HLA-A (Frequency (%)) | |
|---|---|
| HLA-A1 | (25.1) |
| HLA-A2 | (44.8) |
| HLA-A3 | (22.6) |
| HLA-A24 | (18.2) |
| HLA-A11 | (11.8) |
| HLA-A28 | (9.8) |
| HLA-A29 | (10.3) |
| HLA-A32 | (9.8) |
| HLA-B15 | (12.3) |
| HLA-B (Frequency (%)) | |
| HLAB5 | (15.2) |
| HLA-B7 | (18.2) |
| HLA-B8 | (16.7) |
| HLA-B12 | (32.5) |
| HLAB14 | (8.8) |
| HLA-B18 | (11.3) |
| HLA-B35 | (15.2) |
| HLA-B40 | (13.7) |

(from Snell GD et al, Histocompatibility, New York, Academic Press, 1976)

The frequencies with which the various alleles appear in a population is not random; it depends on the racial makeup of the population. Dr. Motomi Mori has determined the frequencies with which thousand of different haplotypes of HLA-A, -B, and -DR loci appear in Caucasian, African-American, Asian-American, and Native American populations. Each haplotype is a particular combination of HLA-A, HLA-B, and HLA-DR loci that is present on a single copy of chromosome no. 6. The frequencies of several relatively common HLA-A, -B, and -DR haplotypes are shown in Table 3 to illustrate the wide variation in HLA haplotype frequencies in some of the racial groups that make up the North American population. In interpreting haplotype frequency data such as that shown in Table 3, one must bear in mind that cells of patients and organs are diploid and have an HLA type that is the product of the HLA haplotypes of the chromosomes inherited from both parents.

TABLE 3

Examples of HLA-A, -B, -DR haplotype frequencies
HLA-A, -B, and -DR haplotype frequencies (expressed in percent) and
their respective rankings within each racial group: Caucasian (CAU),
African-American (AFR), Asian-American (ASI) and Native American (NAT).

| Haplotype | | | Frequency (%) | | | | | Ranking | | | | |
|---|---|---|---|---|---|---|---|---|---|---|---|---|
| A | B | DR | CAU | afr | ASI | LAT | NAT | CAU | AFR | ASI | LAT | NAT |
| 1 | 7 | 2 | 0.5349 | 0.2094 | 0.0798 | 0.1888 | 0.2812 | 21 | 58 | 262 | 91 | 62 |
| 1 | 8 | 3 | 5.1812 | 1.2491 | 0.3195 | 1.6733 | 4.7439 | 1 | 2 | 54 | 3 | 1 |
| 2 | 14 | 1 | 0.1563 | 0.0444 | 0.0076 | 0.3794 | 0.0624 | 107 | 539 | 1451 | 39 | 312 |
| 2 | 35 | 4 | 0.1457 | 0.0737 | 0.3293 | 1.2858 | 0.6342 | 115 | 302 | 49 | 4 | 12 |
| 2 | 35 | 8 | 0.0823 | 0.0931 | 0.1756 | 1.7641 | 0.3289 | 241 | 226 | 122 | 1 | 46 |
| 2 | 44 | 4 | 2.1507 | 0.6506 | 0.1276 | 0.6906 | 2.0004 | 3 | 4 | 170 | 12 | 3 |
| 3 | 7 | 2 | 2.6285 | 0.7596 | 0.1891 | 1.1986 | 2.7083 | 2 | 3 | 113 | 5 | 2 |
| 3 | 7 | 4 | 0.4411 | 0.1534 | 0.0498 | 0.1795 | 0.4448 | 30 | 104 | 408 | 98 | 29 |
| 3 | 7 | 8 | 0.0848 | 0.0367 | 0.0000 | 0.0622 | 0.0537 | 230 | 653 | 14053 | 310 | 366 |
| 3 | 35 | 1 | 1.0224 | 0.2741 | 0.1372 | 0.3552 | 0.8125 | 7 | 29 | 156 | 44 | 8 |
| 31 | 51 | 4 | 0.0915 | 0.0342 | 0.1646 | 0.2597 | 0.5691 | 209 | 699 | 135 | 64 | 16 |
| 32 | 14 | 7 | 0.2617 | 0.0513 | 0.0046 | 0.1324 | 0.1775 | 57 | 479 | 1858 | 140 | 104 |

The data in Table 3 was produced for The National Marrow Donor Program Donor Registry, and is available at the Internet web site of Motomi Mori, Ph.D., Huntsman Cancer Institute, Salt Lake City, Utah.

D. Rejection Triggered by Minor Histocompatibility Antigens:

Matching the MHC molecules of a transplant to those of the recipient significantly improves the success rate of clinical transplantation; however, it does not prevent rejection, even when the transplant is between HLA-identical siblings. This is because rejection is also triggered by differences between the minor histocompatibility antigens. These polymorphic antigens are actually "non-self peptides bound to MHC molecules on the cells of the transplant tissue. The rejection response evoked by a single minor histocompatibility antigen is much weaker than that evoked by differences in MHC antigens, because the frequency of the responding T cells is much lower (Janeway et al., supra, page 525). Nonetheless, differences between minor histocompatibility antigens will often cause the immune system of a transplant recipient to eventually reject a transplant, even where there is a match between the MHC antigens, unless immunosuppressive drugs are used.

E. Inadequate Supply of Cells, Tissues, and Organs for Transplant.

The number of people in need of cell, tissue, and organ transplants is far greater than the available supply of cells, tissues, and organs suitable for transplantation. Under these circumstances, it is not surprising that obtaining a good match between the MHC proteins of a recipient and those of the transplant is frequently impossible, and many transplant recipients must wait for an MHC-matched transplant to become available, or accept a transplant that is not MHC-matched. If the latter is necessary, the transplant recipient must rely on heavier doses of immunosuppressive drugs and face a greater risk of rejection than would be the case if MHC matching had been possible. There is presently a great need for new sources of cells, tissues, and organs suitable for transplantation that are histocompatible with the patients in need of such transplants.

DESCRIPTION OF THE INVENTION

Figure 1:
FIG. 1 shows cynomolgus monkey blastocysts derived from parthenogenetic embryos.

A. A Bank of Stem Cell Lines Homozygous for MHC Loci:

It is an object of the present invention to prepare a bank of totipotent, nearly totipotent, and/or pluripotent stem cell lines that are homozygous for one or more critical antigen genes, i.e., genes which encode histocompatibility antigens, e.g., in the case of human stem cells and "stem-like" cells, MHC alleles that are present in the human population. Preferably, this work will be homozygous for MHC alleles that are representative of at least most prevalent in the particular species, preferably human. Many of these lines will also have an ABO blood group type O-negative to make them broadly compatible across the different blood types. Stem cell lines of the present invention can be induced to differentiate into cell types suitable for therapeutic transplant. Because the cells of the present invention have homozygous MHC alleles, the chance of obtaining cells for transplant that have MHC alleles that match those of a patient in need of a transplant is significantly enhanced. Instead of having to find a six of six match between two sets of HLA-A, HLA-B, and HLA-DR antigens, a high level of histocompatibility is provided by the cells for transplant of the present invention when either of the two HLA-A, HLA-B, and HLA-DR antigens of the prospective transplant recipient matches one of the corresponding homozygous HLA antigens of the cells for transplant. For example, a stem cell bank able to provide cells having an HLA-A/HLA-B match to a patient having any of the eight HLA-A and nine HLA-B antigens listed in Table 2 would require only 72 stem cell lines with homozygous HLA-A and HLA-B antigens; whereas a bank of stem cells with heterozygous HLA-A and HLA-B antigens would need to have 4032 different stem cell lines. To provide a library of heterozygous stem cell lines that match the WHO list of serological types would require obtaining stem cells having every combination of 28 different pairs of HLA-A antigens and 59 different pairs of HLA-B, to account for both the maternal and paternal alleles for each loci. The complexity of such a stem cell bank, i.e., the number of different cell lines required, would be 2,587,032. In contrast, a bank of stem cells homozygous for the same HLA-A and HLA-B antigens would only need to have a complexity of 1,652 stem cell lines to guarantee a match to a patient with HLA-A and -B antigens on the WHO list of serological types. The actual number required to meet the needs of a majority of patients will actually be less than this due to the nonrandom distribution of alleles in various populations around the world. Patients in need of bone marrow stem cell grafts who are homozygous in particular alleles are particularly sensitive to graft versus host disease when heterozygous bone marrow grafts are used. Stem cell grafts using stem cells having homozygous alleles made according to the methods of the present invention would alleviate this common complication of transplants.

This present invention provides novel means for making libraries of totipotent and/or pluripotent stem cells that can serve as sources of cells for therapeutic transplant that are highly histocompatible with human or nonhuman patients in need of cell transplants. Additionally, those cell lines are useful in creating animal models for specific diseases that may be used to evaluate potential treatments and drug antidotes. In one embodiment, the invention comprises preparing a bank of stem cell lines that are homozygous for one or more critical antigen alleles, in the case of human stem cells. MHC alleles that are present in all or most of the world's populations, including the populations of North America, Central and South America, Europe, Africa, and Asia, and the Pacific islands. It is an object of the present invention to provide a stem cell bank comprising stem cells generated from vertebrate somatic cells, preferably mammalian somatic cells, and more preferably human research cells that are homozygous for one or more critical antigen alleles, e.g., MHC alleles using nuclear transfer or parthenogenic produced embryos. A preferred object of the present invention is to provide a stem cell bank comprising diploid vertebrate, preferably mammalian and more preferably human stem cells generated by parthenogenesis that are homozygous for MHC alleles. Another object of the present invention is to provide a stem cell bank comprising diploid vertebrate, preferably mammalian and more preferably human stem cells generated by union of sperm and egg in vitro that are homozygous for one or more MHC alleles. S&M further, an object of the invention is to preview a bank of homozygous IES cell lines by introducing cytoplasm from embryonic cells into growth cells that are homozygous for specific MITC allele or are rendered homozygous by genetic manipulation. (The embryonic cytoplasm contains constituents that de-differentiate the differentiated growth cell into stem cell lineages.

The stem cell bank of the present invention comprises lines of totipotent, nearly totipotent, and/or pluripotent stem cells that are homozygous for at least one histocompatibility antigen collection. In the case of human stem cells this will be an MHC allele selected from the group consisting of HLA-A, HLA-B, HLA-C, HLA-DR, HLA-DQ, and HLA-DP. In a useful embodiment, the stem cell bank comprises totipotent, nearly totipotent, and/or pluripotent stem cells stem cells that are homozygous for the significant histocompatibility antigen alleles, e.g., the HLA-A. HLA-B, and HLA-DR alleles. In another embodiment, the stem cell bank comprises stem cells that are homozygous for all of the histocompatibility antigen alleles, e.g., MHC alleles.

The stem cell bank of the present invention comprises totipotent and/or nearly totipotent stem cells such as embryonic stem (ES) cells, that can differentiate in vivo or ex vivo into a wide variety of different cell types having one or more homozygous MHC alleles. The stem cell bank of the present invention can also comprise partially differentiated, pluripotent stem cells such as neuronal stem cells and/or hematopoietic stem cells, that differentiate in vivo or ex vivo into a more limited number of differentiated cell types having one or more homozygous MHC alleles. These stem cells optionally may be transgenic, e.g., they may express antigens that encode therapeutic or diagnostic proteins and polypeptides. For example, the stem cells may be genetically engineered to express proteins that inhibit immune rejection responses such as CD4O-L (CD154 or gp139) or in the case of porcine stem cells May be genetically engineered to knock-out a glycosylated antigen that is known to trigger immune rejection responses.

An object of the present invention is to provide a stem cell bank comprising stem cells having homozygous histocompatibility alleles, i.e., MHC alleles that are available "off the shelf" for providing histocompatible cells suitable for transplant to patients in need of such a transplant. Desirably, this stem bank will include stem cell lines that are representative of the different histocompatibility antigens expressed in the particular species, e.g., human. In a useful embodiment, the stem cell bank comprises stem cells that are isolated and maintained without feeder cells or serum of non-human animals, to minimize concerns of contamination by pathogens. In another useful embodiment, the stem cell bank comprises stem cells that are genetically modified relative to the cells of the donor, e.g., human donor from which they are derived. In another embodiment, the stem cell bank comprises stem cells generated by nuclear transfer techniques that are rejuvenated, or "hyper-youthful," relative to the cells of the donor, e.g., non-human mammal or human donor from which they are derived, and also relative to age-matched control cells of the same type and species that are not generated by nuclear transfer techniques. Such rejuvenated or "hyper-youthful" cells have extended telomeres, increased proliferative life-span, and metabolism that is more characteristic of youthful cells, e.g., increased EPC-1 and telomerase activities, relative to the human donor cells from which they are derived, and also relative to age-matched control cells of the same type that are not generated by nuclear transfer techniques.

Another object of the present invention is to provide a stem cell bank comprising stem cells having homozygous recessive alleles responsible for genetically inherited diseases. Recessive disease-causing genes are endemic in the population, and such stem cells can be generated by parthenogenesis using oocytes collected from female carriers of the recessive disease-causing alleles. There is great need for totipotent, nearly totipotent, and/or pluripotent stem cells that having homozygous recessive disease-causing alleles that can be induced to differentiate into cells useful for basic research directed to studying the disease phenotype, both ex vivo and in vivo (e.g., in immunodeficient laboratory animals), and for screening to discover drugs and other therapies that treat or cure the disease.

B. Terms Used in Describing the Invention:

As used herein, a "stem cell" is a cell that has the ability to proliferate in culture, producing some daughter cells that remain relatively undifferentiated, and other daughter cells that give rise to cells of one or more specialized cell types; and "differentiation" refers to a progressive, transforming process whereby a cell acquires the biochemical and morphological properties necessary to perform its specialized functions. Stem cells therefore reside immediately antecedent to the branch points of the developmental tree.

As used herein, a "totipotent" cell is a stem cell with the "total power to differentiate into any cell type in the body, including the germ line following exposure to stimuli like that normally occurring in development. Examples of totipotent cells include an embryonic stem (ES) cell, an embryonic germ (EG) cell, an inner cell mass (ICM)-derived cell, or a cultured cell from the epiblast of a late-stage blastocyst.

As used herein, a "nearly totipotent cell" is a stem cell with the power to differentiate into most or nearly all of the cell types in the body following exposure to stimuli like that normally occurring in development.

As used herein, a "pluripotent cell" is a stem cell that is capable of differentiating into multiple somatic cell types, but not into most or all cell types. This would include by way of example, but not limited to, mesenchymal stem cells that can differentiate into bone, cartilage and muscle; hematopoietic stem cells that can differentiate into blood, endothelium, and myocardium; neuronal stem cells that can differentiate into neurons and glia; and so on.

As used herein, an "embryonic stem cell line is a cell line" with the characteristics of the murine ES cells isolated from morulae or blastocyst inner cell masses, as reported by Martin (Proc. Natl. Acad. Sci. USA (1981) 78:7634-7638); and by Evans et al. (Nature (1981) 292: 154-156). ES cells have high nuclear-to-cytoplasm ratio, prominent nucleoli, are capable of proliferating indefinitely and can be differentiate into most or all of the specialized cell types of an organism, such as the three embryonic germ layers, all somatic cell lineages, and the germ line. ES cells that can differentiate into all of the specialized cell types of an organism are totipotent. In some cases, ES cells are obtained that can differentiate into almost all of the specialized cell types of an organism; but not into one or a small number of specific cell types. For example, Thomson et al. describe isolating a primate ES cell that, when transferred into another blastocyst, does not contribute to the germ line (Proc. Natl. Acad. Sci. USA. (1995) 92:7844-7848). Such ES cells are an example of stem cells that are nearly totipotent.

As used herein, "inner cell mass-derived cells" (ICM-derived cells) are cells directly derived from isolated ICMs or morulae without passaging them to establish a continuous ES or ES-like cell line. Methods for making and using ICM-derived cells are described in co-owned U.S. Pat. No. 6,235,970, the contents of which are incorporated herein in their entirety.

As used herein, "enucleation" refers to removal of the genomic DNA from an cell, e.g., from a recipient oocyte. Enucleation therefore includes removal of genomic DNA that is not surrounded by a nuclear membrane, e.g., removal of chromosomes aligned to form a metaphase plate. As discussed below, the recipient cell can be enucleated by any of the known means either before, concomitant with, or after nuclear transfer.

As used herein, "ex vivo" cell culture refers to culturing cells outside of the body. Ex vivo cell culture includes cell culture in vitro, e.g., in suspension, or in single- or multi-well plates. Ex vivo culture also includes co-culturing cells with two or more different cell types, and culturing in or on 2- or 3-dimensional supports or matrices, including methods for culturing cells alone or with other cell types to form artificial tissues.

As used herein, "parthenogenetic embryos" refers to an embryo that only contains male or female chromosomal DNA that is derived from male or female gametes. For example, parthenogenetic embryos can be derived by activation of unfertilized female gametes, e.g., unfertilized human, murine, cynomolgus or rabbit oocytes.

As used herein, "nuclear transfer embryo" refers to an embryo that is produced by the fusion or transplantation of a donor cell or DNA from a donor cell into a suitable recipient cell, typically an oocyte of the same or different species that is treated before, concomitant or after transplant or fusion to remove or inactivate its endogenous nuclear DNA. The donor cell used for nuclear transfer include embryonic and differentiated cells, e.g., somatic and germ cells. The donor cell may be in a proliferative cell cycle ($G_1$, $G_2$, S or M) or non-proliferating ($G_o$ or quiescent). Preferably, the donor cell or DNA from the donor cell is derived from a proliferating mammalian cell culture, e.g., a fibroblast cell culture. The donor cell optionally may be transgenic, i.e., it may comprise one or more genetic addition, substitution or deletion modifications.

As used herein, the term "gene" refers to the nucleotide sequences at a genetic locus that encode and regulate expression of a functional mRNA molecule or a polypeptide; i.e., as used herein, a gene includes the nucleotide sequences that make up the coding sequence (exons and introns), the promoter, enhancers, and other DNA elements that regulate transcription, including as elements conferring cell type-specific and differentiation stage-specific expression, hormone responsive elements, repressor elements, etc., and nucleotide sequences that encode signals that regulate splicing and translation of the mRNA, such as a cleavage signal, a polyadenylation signal, or an internal ribosome entry site (IRES).

C. Providing Histocompatible Transplants to Animal or Human Recipients:

Another object of the invention is to provide a method by which a human or non-human animal, e.g., a person in need of a cell or tissue transplant can be provided with cells or tissue suitable for transplantation that have homozygous histocompatibility antigen alleles, e.g., in the case of human recipients MHC alleles that match the MHC alleles of the person needing the transplant. The invention provides a method in which the MHC alleles of a person in need of a transplant (the recipient) are identified, and a line of stem cells homozygous for at least one MHC allele present in the recipients cells is obtained from a stem cell bank produced according to the disclosed methods. That line of stem cells is then used to generate cells or tissue suitable for transplant that are homozygous for at least one MHC allele present in the recipients cells. The method of the present invention further comprises grafting the cells or tissue so obtained to the body of the person in need of such a transplant. In a useful embodiment of the invention, three, four, five, six or more of the MHC alleles of the line of stem cells used to generate cells or tissue for transplant are homozygous and match MHC alleles of the transplant recipient.

In a useful embodiment, the line of stem cells used to generate cells or tissue suitable for transplant is a line of totipotent or nearly totipotent embryonic stem cells. In another useful embodiment, the line of stem cells used to generate cells or tissue suitable for transplant is a line of hematopoietic stem cells. The lines of stem cells that can be used to generate cells or tissue suitable for transplant are available "off the shelf" in the stem cell bank of the present invention. In a useful embodiment, the stem cell bank of the present invention comprises lines of totipotent, nearly totipotent, and/or pluripotent stem cells that are lines of rejuvenated, "hyper-youthful cells" generated by nuclear transfer techniques. In another useful embodiment, the stem cell bank of the present invention comprises one or more lines of totipotent, nearly totipotent, and/or pluripotent stem cell having DNA that is genetically modified relative to the DNA of the human donor from which they are derived. For example, the invention comprises altering genomic DNA of the cells to replace a non-homozygous MHC allele with one that is homozygous, or to inhibit the effective presentation of a class I or class II HLA antigen on the cell surface, e.g., by preventing expression of β2-microglobulin, or by preventing expression of one or more MHC alleles. Also, the invention encompasses introducing one or more genetic modifications that result in lineage-defective stem cells, i.e., stem cells which cannot differentiate into specific cell lineages.

D. Methods for Making Stem Cell Lines with Homozygous MHC Alleles:

Totipotent, nearly totipotent, and/or pluripotent stem cell lines that make up the stem cell banks of the present invention can be derived from blastocyst embryos made up of cells that are homozygous for some or all of the histocompatibility antigen alleles, e.g., MHC alleles. Blastocyst embryos useful for the present invention can be made by several different methods. In preferred embodiments of the invention, human embryos are produced by fertilization, parthenogenesis, or by same or cross-species somatic cell nuclear transfer. In the case of human embryos, for ethical reasons, they are never allowed to develop beyond the stage of pre-implantation blastocysts of about 9-10 days before the inner cell mass cells are isolated and are cultured to produce embryonic stem (ES) cells. The cloning methods of the present invention which utilize human embryos are restricted to human therapeutic cloning techniques. The present invention does not include any methods that permit development of human embryos beyond the pre-implantation stage of about 9-10 days, nor does it include or contemplate reproductive cloning in any form.

Stem Cells from Embryos Produced by Union of Sperm and Egg:

In one embodiment of the invention, human or non-human stem cells are derived from embryos produced in vitro by uniting sperm and eggs by known means; for example, by in vitro fertilization (IVF) or by intracytoplasmic sperm injection (ICSI). To produce cells having homozygous MHC alleles, sperm and eggs can be obtained from individuals that are closely related; e.g., brother and sister or one determined to have similar MHC alleles. As in HLA typing for a transplant between siblings, there is about a 25% chance that an embryo produced with sibling's gametes will have matching HLA loci. The embryos produced by uniting sperm and eggs of related individuals are cultured in vitro to produce early embryo including blastocysts from which ES cells or inner cell masses are derived. HLA types of the resulting pluripotent cell lines are determined by known means; e.g., by PCR, or by culturing a sample of the cells under conditions that induce differentiation, and performing serological testing of the cells using antibodies against specific HLA antigens. Pluripotent cell lines having one or more homozygous MHC alleles are then selected for inclusion in the stem cell bank. Embryos produced by union of sperm and egg have normal genetic imprinting, i.e., they have the epigenetic contributions of both male and female parents, so they develop to form blastocysts from which pluripotent cells can be derived with high efficiency.

In the case where sperm and egg donors are not closely related sperm can be banked from individuals with characterized MHC loci and used for IVF or ICSI fertilization of oocytes that also have characterized MHC loci to produce embryos and stem cells with a high likelihood of generating homozygosity in the MHC loci.

Persons skilled in the art would recognize that the human embryos produced by uniting sperm and eggs of closely related individuals according to the present invention may be viable and could be implanted into human females to make pregnancies and develop to live births of humans having homozygous HLA alleles. This would be highly unethical, in view of the known risks to the health of the child that result from close inbreeding. As stated above, the present invention expressly does not comprise allowing the embryos to develop beyond blastocysts of about 9-14 days.

Stem Cells Produced by Parthenogenesis:

In another embodiment of the invention, totipotent and pluripotent human stem cells are derived from embryos produced by parthenogenesis. The stem cells obtained by this method are diploid, because extrusion of the second polar body following parthenogenetic activation is inhibited. Methods for producing a diploid human embryo by parthenogenesis, for culturing the embryo in vitro to form a blastocyst, and for culturing cells of the blastocyst to obtain stem cells, are described in co-owned and co-pending PCT Application PCT/US02/37899 (Methods for Making and Using Reprogrammed Human Somatic Cell Nuclei and Autologous and Isogenic Stem Cells) filed Nov. 26, 2002, the disclosure of which is incorporated herein by reference in its entirety. Similar methods for producing diploid embryos by parthenogenesis using oocytes of rhesus monkeys and cynomolgus monkeys have been described by Mitalipov et al. (2001, Biology of Reproduction, 65:253-259) and Cibelli et al. (2002. Science, 295:81), respectively, the contents of both of which are incorporated herein by reference in their entirety.

In general, production of a diploid human embryo by parthenogenesis comprises a. obtaining oocytes from human donors induced to superovulate by treatment with gonadotropins followed by hCG injection;

b. activating the oocytes at about 38-45 hours after hCG stimulation;

c. exposing the activated oocytes to. chemical treatment that inhibits extrusion of the second polar body; and d. culturing the embryo in vitro under conditions resulting in formation of a blastocyst.

Oocyte activation is normally mediated by oscillations of intracellular $Ca^{+2}$ ion triggered by the sperm cell. Parthenogenetic activation of the oocytes can be achieved by any of the known means for inducing oocyte activation. Such methods generally involve exposing the oocyte to ethanol, electroporation, calcium ionophore, ionomycin, inositol 1,4,5-triphosphate to increase the intracellular $Ca^{+2}$ ion concentration in the oocyte, in combination with a treatment that temporarily inhibits protein synthesis or protein phosphorylation. For example, Mitalipov et al. (supra, p. 254) describe two such methods that result in production of diploid parthenogenetic blastocysts from oocytes of rhesus monkeys. In one method, the oocytes are incubated briefly in medium containing ionomycin and calcium, followed by incubation for several hours in medium containing 6-aminomethylpurine (DMAP), an inhibitor of protein phosphorylation. In the other method, the oocytes are electroporated three times in medium containing calcium, and between each electroporation, the oocytes are incubated for about 30 minutes in medium containing cycloheximide, an inhibitor of protein synthesis, and cytochalasin B, an inhibitor of microfilament synthesis.

Using a similar method Cibelli et al. (supra) parthenogenetically activated oocytes of a cynomolgus monkey; cultured the activated oocytes in vitro to produce a diploid blastocysts; and isolated a line of diploid ES cells from cells of the inner cell mass of a parthenogenesis-derived embryo; and showed that the ES cells are capable of differentiating into cell types of all three embryonic germ layers. This is also described in U.S. Ser. No. 09/697,297 by Cibelli et al, which is incorporated by reference in its entirety here.

Oocytes are obtained from women having MHC alleles of the type needed for the stem cell bank. The oocytes are parthenogenetically activated and are cultured to form blastocysts. Using known methods, the inner cell mass cells of the blastocysts are cultured in vitro to generate diploid embryonic stem cells. Because extrusion of the second polar body after meiosis II was prevented, the homologous chromosomes of such ES cells are actually the sister chromatids that were joined together as a dyad during meiosis I. Since the sister chromatids were formed by replication of a single set of chromosomes at the outset of meiosis, they will have identical DNA sequences, except for those regions that were exchanged with the homologous dyad during the recombination stage of meiosis. The HLA genes of the MHC are tightly linked, and recombination in this region is rare occurring with a frequency of about 1%. The two sets of homozygous HLA alleles in the parthenogenetically-derived stem cell lines obtained with oocytes from a given donor reflect the HLA haplotypes of the maternal and paternal copies of chromosome 6 that the donor inherited from her parents. Known screening methods can be performed to identify the cell lines that have non-homozygous HLA antigens due to genetic recombination, and to identify the homozygous HLA alleles of each stem cell line.

Stem Cells Produced by Haplodization:

In another embodiment of the invention, totipotent and pluripotent human stem cells are derived from embryos produced by union of two haploids that are homozygous for one or more MHC alleles.

Methods for producing embryos by fusion of two haploid genomes are described in U.S. Ser. No. 10/344,724, filed on Feb. 14, 2003 entitled, "Use of Haploid Genomes for Genetic Diagnosis, Modification and Multiplications", which is incorporated by reference in its entirety herein.

A bank of stem cell lines according to the present invention can be obtained by screening the population- and -identifying individuals having cells which express desired MHC antigens, and obtaining donations of the somatic cells from these individuals. However, individuals that are homozygous for MHC antigens are rare, because they are only found in inbred population. Thus, the useful embodiment of the invention is utilization of heterozygous donor cells to create homozygous stem cells.

In this method, somatic cells are introduced into enucleated human oocytes, and the newly constructed oocytes are activated to induce haplodization (Tesarik et al., 2001 RB Online. 2:160-164), Lachem-Kaplan et al, 2001 RB Online 3: 205-211. When a protocol for primate oocyte activation are used, approximately 90% of eggs yield pseudo-polar body (Shoukhrat et al, 2001 Biol Reprod 65:253-259). These pseudo-polar bodies are used for genotyping using well established techniques. Other haploid embryos also can be constructed by transferring cells from other donors using the same protocol. Or the donor oocytes can be screened for the presence of desired MHC allele after activation to generate haploid oocytes. Screening of the first polar bodies will reveal the genotype of the oocytes as in above the reconstructed eggs. The activation can be done chemically and/or by injecting sperm factors (see U.S. Application No. 60/191,089 of Rafael Fissore filed Mar. 22, 2000 incorporated by reference in its entirety herein) easily unless $2^{nd}$ polar body extrusion is blocked systematically (incorporated by reference in its entirety herein). The remaining pronuclei are transferred to construct diploid embryos by pronuclear transfer techniques. These techniques have been well established and used widely in developmental biology fields for more than a decade. To avoid possible imprinting disturbance, morula stage human embryo lysates are injected into the newly constructed eggs. These embryo lysates are known to have ability to modify imprinting status of murine androgenone so effectively to make live born animals, otherwise develop very poorly in vitro and died out after implantation (Hagemman and First, 1992 Development 114:997-1001)

More particularly, the invention includes methods for generating stem cells by haplodization comprising the steps of:

a. Inserting a somatic donor cell, or the nucleus of such a cell, into an oocyte that is free of oocyte genomic DNA.

b. Activation of the reconstructed embryos to expel haploidal genome into a pseudopolar_body.

c. Screening of the pseudopolar_body for the genotyping of remaining pronucleus.

d. Union of the two pronuclei to generate diploid embryos by pronuclei transfer. Or alternatively, transferring a pronucleus to an activated haploid oocyte which has desired haploid genome e. Injection of human morular stage embryo lysates to the reconstructed embryos.

f. Culturing embryo and generating stem cells/or differentiated cells or tissue needed for transplant from cells of said embryos.

In addition, haploid genomes can be derived by other means known in the art, including the use of the first and second polar bodies. While occasionally, such DNA is fragmented, intact genomes can be obtained as evidenced by the production of live mice from polar body DNA (Wakayama, T., and Yanagimachi, R. Biol. Reprod. 1998. 59(1) 100-4) and these haploid or diploid genomes can be used as described above.

Stem Cells Produced by Cytoplasm Transfer:

Totipotent and pluripotent stem cells homozygous for histocompatibility antigens, e.g., MHC antigens can also be produced by transferring cytoplasm from an oocyte or an ES cell into a somatic cell that is homozygous for MHC antigens, so that the chromatin of the somatic cell is reprogrammed and the somatic cell de-differentiates to generate a pluripotent or totipotent stem cell. Methods for converting differentiated cells into de-differentiated, pluripotent, stem or stem-like cells that can be induced to re-differentiate into a cell type other than that of the initial differentiated cells, are described in co-owned and co-pending U.S. application Ser. No. 09/736,268, filed Dec. 15, 2000, and U.S. application Ser. No. 10/112,939 filed Apr. 2, 2002, both by Karen B. Chapman, the disclosures of both of which are incorporated herein by reference in their entirety.

Stem Cells from Embryos Produced by Nuclear Transfer:

In another embodiment of the invention, totipotent, nearly totipotent, and/or pluripotent human stem cells that are homozygous for one or more MHC alleles are derived from embryos produced in vitro by somatic cell nuclear transfer techniques. The totipotent and/or pluripotent stem cells generated by this embodiment of the invention will have the genomic DNA of the somatic donor cell used for nuclear transfer. When the somatic donor cell is homozygous for an MHC allele, the stem cells generated by nuclear transfer cloning will also be homozygous for the MHC allele.

A bank of stem cell lines according to the present invention can be obtained by screening a species, preferably human population and identifying individuals that are homozygous for clinical MHC antigens, and obtaining donations of somatic cells from these individuals. Individuals having homozygous MHC alleles are often found in inbred populations. Alternatively, somatic cells, preferably human, homozygous for MHC loci that are useful for the present invention can be produced by obtaining somatic cells that are heterozygous for an MHC allele, and genetically altering the DNA of the cells using known methods so that they are homozygous for one or more MHC loci. This can be done, for example, by using well-known homologous recombination techniques to replace a non-homozygous MHC allele with one that is homozygous.

In a useful embodiment of the invention, donors of somatic cells to be used in nuclear transfer according to the present invention may be selected to provide cells that are relatively resistant to blood cell cancers, for use in reconstituting the blood of blood cancer patients. Such blood cells can be chosen based on their natural killer (NK) cell phenotype. The somatic cell donors who having resistance to blood cell cancers can be selected to have homozygous MHC alleles, or the donated cells can be genetically altered to have one or more homozygous MHC alleles as discussed above.

The donated cells are cloned by nuclear transfer techniques that result in production of blastocyst embryos from which are obtained totipotent and/or pluripotent stem cells that are homozygous for one or more MHC loci. For each cell line to be produced, a somatic donor cell that is homozygous for a MHC allele, or the nucleus or set of chromosomes of such a cell, is inserted into a human oocyte that is coordinately enucleated to produce a nuclear transfer unit that develops as an embryo. The embryo is cultured ex vivo to the blastocyst stage, and totipotent and/or pluripotent stem cells are derived from inner cell mass (ICM) cells of the embryo that have the genomic DNA of the donor cell. In a useful embodiment, the stem cell bank comprises totipotent, nearly totipotent ES cells homozygous for MHC antigens. Totipotent and pluripotent stem cells homozygous for various combinations of MHC antigens are assembled and maintained as a bank of cells available for therapeutic transplantation.

Methods for transferring the nuclear DNA of a somatic cell of a patient into an oocyte to effect the reprogramming of the chromatin and produce an NT unit from which are generated pluripotent stem cells and totipotent ES cells are described, for example, in co-owned and co-pending U.S. application Ser. No. 09/655,815 filed Sep. 6, 2000; and U.S. application Ser. No. 09/797,684 filed Mar. 5, 2001; and also in PCT Application No. PCT/US02/37899 (Methods for Making and Using Reprogrammed Human Somatic Cell Nuclei and Autologous and Isogenic Stem Cells) filed Nov. 26, 2002, the disclosures of all three of which are incorporated herein by reference in their entirety. Similar methods are described in co-owned and co-pending U.S. application Ser. No. 09/527,026 filed Mar. 16, 2000, Ser. No. 09/520,879 filed Apr. 5, 2000, and Ser. No. 09/656,173 filed Sep. 6, 2000, the disclosures of which are incorporated herein by reference in their entirety. In general, methods for cloning by somatic cell nuclear transfer to produce stem cells for generating cells or tissue useful for transplantation comprise the steps of:

a. inserting a somatic donor cell, or the nucleus of such a cell, into an oocyte and removing the oocyte genomic DNA (enucleation) under conditions that produce an activated nuclear transfer unit that develops as an embryo; and b. generating stem cells and/or differentiated cells or tissue needed for transplant from cells of said embryo.

Such a method can be used to generate lines of totipotent or nearly totipotent ES cells that can be cultured under conditions in which they differentiate into specific, recognized cell types. Such ES cells have the capacity to differentiate into every cell type of the body, including the germ cells. The stem cells produced by somatic cell nuclear transfer have the patients genomic DNA, so the differentiated cells and tissues generated from such stem cells are nearly completely autologous—all of the cells' proteins, are encoded by the patients own DNA except for those proteins encoded by the cells' mitochondria, which derive from the oocyte. Accordingly, differentiated cells and tissues generated from stem cells produced by nuclear transfer methods can be transplanted to the person who provided the nuclear donor cell without triggering the severe rejection response that results when foreign cells or tissue are transplanted.

As described in the above-identified co-pending applications, the somatic donor cell used for nuclear transfer to produce human stem cells homozygous for a MHC allele according to the present invention can be of any. somatic cell type in the body. For example, the somatic donor cell can be a cell selected from the group consisting of fibroblasts. B cells, T cells, dendritic cells, keratinocytes, adipose cells, epithelial cells, epidermal cells, chondrocytes, cumulus cells, neural cells, glial cells, astrocytes, cardiac cells, esophageal cells, muscle cells, melanocytes, hematopoietic cells, macrophages, monocytes, and mononuclear cells. The somatic donor cell can be obtained from any organ or tissue in the body; for example, it can be a cell from an organ selected from the group consisting of liver, stomach, intestines, lung, stomach, intestines, lung, pancreas, cornea, skin, gallbladder, ovary, testes, kidneys, heart, bladder, and urethra.

Methods for generating rejuvenated, "hyper-youthful" stem cells and differentiated somatic cells having the genomic DNA of a human somatic donor cell are described in co-owned and co-pending U.S. application Ser. No. 09/527,026 filed Mar. 16, 2000, Ser. No. 09/520,879 filed Apr. 5, 2000, and Ser. No. 09/656,173 filed Sep. 6, 2000, the disclosures of which have been incorporated herein by reference in their entirety. For example, rejuvenated, "hyper-youthful" stem cells having the genomic DNA of a human somatic cell donor can be produced by a method comprising:

a. isolating normal, somatic cells from a human donor, and passaging or otherwise inducing the cells into a state of checkpoint-arrest, senescence, or near-senescence, b. transferring a checkpoint-arrested, senescent, or near-senescent donor cell, the nucleus of said cell, or chromosomes of said cell, into a recipient oocyte, and coordinately removing the oocyte genomic DNA from the oocyte, to generate an embryo; and c. generating rejuvenated stem cells from said embryo having the genomic DNA of the donor cell.

As described in the above-identified co-pending applications, the pluripotent and totipotent stem cells homozygous for a MHC allele of the present invention that are produced by nuclear transfer using a checkpoint-arrested, senescent, or near-senescent donor cell are rejuvenated cells that are distinguished from other cells in having telomeres that are longer than the corresponding telomeres of the checkpoint-arrested, senescent, or near-senescent donor cell. Moreover, the telomeres of such rejuvenated cells are on average at least as long as the telomeres of age-matched control cells of the same type and species that are not generated by nuclear transfer techniques. In addition, the nucleotide sequences of the tandem $(TTAGGG)_n$ repeats that comprise the telomeres of such rejuvenated cells are more uniform and regular; i.e., have significantly fewer non-telomeric nucleotide sequences, than are present in the telomeres of age-matched control cells of the same type and species that are not generated by nuclear transfer. Such rejuvenated cells are "hyper-youthful", in that the proliferative life-span of the rejuvenated cells is at least as long as, and is typically longer than, the proliferative life-span of age-matched control cells of the same type and species that are not generated by nuclear transfer techniques. Such rejuvenated cells also have patterns of gene expression that are characteristic of youthful cells; for example, activities of EPC-1 and telomerase in such rejuvenated cells are typically greater than EPC-1 and telomerase activities in age-matched control cells of the same type and species that are not generated by nuclear transfer techniques.

As described in the above-identified co-pending applications, rejuvenated totipotent and/or pluripotent stem cells can be generated from an embryo produced by nuclear transfer by methods comprising obtaining a blastocyst, an embryonic disc cell, inner cell mass cell, or a teratoma cell using said embryo, and generating the pluripotent and/or totipotent stem cells from said blastocyst, inner cell mass cell, embryonic disc cell, or teratoma cell.

As described in co-owned and co-pending U.S. application Ser. No. 09/685,061 filed Oct. 6, 2000, Ser. No. 09/809,018 filed Mar. 16, 2001, and Ser. No. 09/874,040 filed Jun. 6, 2001, the recipient oocyte may be derived from a non-human mammal. For example, the oocyte may be from a mammal selected from the group consisting of sheep, bovines, bovines, pigs, horses, rabbits, guinea pigs, mice, hamsters, rats, and non-human primates. In a preferred embodiment, the oocyte is from a bovine mammal, or a rabbit. A stem cell line having the genome of a human cell that is derived using a nonhuman oocyte is referred to herein as a "human" stem cell line, even though the mitochondria of such cells are of a non-human type.

Genetically Modified Stem Cells:

The methods of the present invention include producing totipotent and/or pluripotent stem cells homozygous for MHC antigens that are genetically modified relative to the cells of the human donor from which they were originally obtained. The stem cells can be genetically modified in any manner that enhances or improves the overall efficiency by which cells for transplant are produced and the therapeutic efficacy of the cell transplantation. Methods that use recombinant DNA techniques to introduce modifications at selected sites in the genomic DNA of cultured cells are well known. Such methods can include (1) inserting a DNA sequence from another organism (human or non-human) into target nuclear DNA, (2) deleting one or more DNA sequences from target nuclear DNA, and (3) introducing one or more base mutations (e.g., site-directed mutations) into target nuclear DNA. Such methods are described, for example, in Molecular Cloning, a Laboratory Manual, 2nd Ed., 1989, Sambrook, Fritsch, and Maniatis, Cold Spring Harbor Laboratory Press; U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos," all of which are incorporated by reference herein in their entirety. Such methods include techniques for transfecting cells with foreign DNA fragments and the proper design of the foreign DNA fragments such that they effect insertion, deletion, and/or mutation of the target DNA genome. For example, known methods for genetically altering cells that use homologous recombination can be used to insert, delete, or rearrange DNA sequences in the genome of a cell of the present invention. A genetic system that uses homologous recombination to modify targeted DNA sequences in a mammalian cell to "knock-out" a cell's ability to express a selected gene is disclosed by Capecchi et al. in U.S. Pat. Nos. 5,631,153 and 5,464,764, the contents of which are incorporated herein in their entirety. Such known methods can be used to insert into the genomic DNA of a cell an additional (exogenous) DNA sequence comprising an expression construct containing a gene that is to be expressed in the modified cell. The gene to be expressed can be operably linked to any of a wide variety of different types of transcriptional regulatory sequences that regulate expression of the gene in the modified cell. For example, the gene can be under control of a promoter that is constitutively active in many different cell types, or one that is developmentally regulated and is only active in one or a few specific cell types. Alternatively, the gene can be operably linked to an inducible promoter that can be activated by exposure of the cell to a physical (e.g., cold, heat, light, radiation) or chemical signal. Many such inducible promoters and methods for using them effectively are well known. Examples of the characteristics and use of such promoters, and of other well-known transcriptional regulatory elements such as enhancers, insulators, and repressors, are described, for example, in Transgenic Animals, Generation and Use, 1997, edited by L. M. Houdebine, Hardwood Academic Publishers, Australia, the contents of which are incorporated herein by reference.

Stem cells homozygous for MI-IC antigens that have multiple genetic alterations can be produced using known methods. For example, one can produce cells that are modified at multiple loci, or cells that are modified at a single locus by complex genetic alterations requiring multiple manipulations. To produce stem cells having multiple genetic alterations, it is useful to perform the genetic manipulations on somatic cells cultured in vitro, and then to clone the genetically altered cells by somatic cell nuclear transfer and generate ES cells having multiple genetic alterations from the resulting blastocysts. Methods for generating genetically modified cells using nuclear transfer cloning techniques are described, for example, in co-owned and co-pending U.S. application Ser. No. 09/527,026 filed Mar. 16, 2000, Ser. No. 09/520,879 filed Apr. 5, 2000, and Ser. No. 09/656,173 filed Sep. 6, 2000, the disclosures of which have been incorporated herein by reference in their entirety.

Alternatively, the totipotent and/or pluripotent stem cells having homozygous MHC alleles that are produced by any of the methods described above can be genetically modified directly using known methods. For example, Zwaka et al. have described a method for genetically modifying human ES cells in vitro by homologous recombination (Nature Biotechnology, Vol. 21, No. 3, March, 2003).

In generating stem cells by nuclear transfer, it is useful to genetically modify the nuclear donor cell to enhance the efficiency of embryonic development and the generation of ES cells. The gene products of the Ped type, which are members of the Class I MHC family and include the Q7 and Q9 genes, are reported to enhance the rate of embryonic development. Modification of the DNA of nuclear donor cells by insertion of DNA expression constructs that provide for the expression of these genes, or their human counterparts, will give rise to nuclear transfer embryos that grow more quickly. It appears that these genes are only expressed early in blastocyst development and so are not expected to be disruptive of later development.

The efficiency of embryonic development can also be enhanced by genetically modifying the nuclear donor cell to have increased resistance to apoptosis. Genes that induce apoptosis are reportedly expressed in preimplantation stage embryos (Adams et al, *Science,* 281(5381):1322-1326 (1998). Such genes include Bad, Bok, BH3, Bik, Hrk, BNIP3, Bim$_L$, Bad, Bid, and EGL-1. By contrast, genes that reportedly protect cells from programmed cell death include BcL-XL, Bcl-w, Mcl-1, A1, Nr-13, BHRF-1, LMW5-HL, ORF16, Ks-Bel-2, E1B-19K, and CED-9. Nuclear donor cells can be constructed in which genes that induce apoptosis are "knocked out" or in which the expression of genes that protect the cells from apoptosis is enhanced or turned on during embryonic development. Expression constructs that direct synthesis of antisense RNAs or ribozymes that specifically inhibit expression of genes that induce apoptosis during early embryonic development can also be inserted into the DNA of nuclear donor cells to enhance development of nuclear transfer-derived embryos. Apoptosis genes that may be expressed in the antisense orientation include BAX, Apaf-1, and capsases. Many DNAs that promote or inhibit apoptosis have been reported and are the subject of numerous patents. The construction and selection of genes that affect apoptosis, and of cell lines that express such genes, is disclosed in U.S. Pat. No. 5,646,008, the contents of which are incorporated herein by reference.

Stem cells can be produced that are genetically modified grow more efficiently in tissue culture than unmodified cells; e.g., by increasing the number of growth factor receptors on the cells' surface. Use of stem cells having such modifications reduces the time required to generate an amount of cells for transplant that is sufficient to have therapeutic effect.

The histocompatibility of a line of cells to be used for transplant with a patient in need of such as transplant may be increased by altering the genomic DNA of the cells to replace a non-homozygous MHC allele with one that is homozygous and matches an HLA allele of the patient. Alternatively, the genomic DNA of the cells can be modified to inhibit the effective presentation of a class 1 or class II HLA antigen on the cell's surface; for example, by introducing a genetic alteration that prevents expression of /32-microglobulin, which is an essential component of class I HLA antigens; by introducing genetic alterations in the promoter regions of the class I and/or or class II MHC genes; or simply by deleting a portion of the DNA of one or more of the class I and/or or class II MHC genes sufficient to prevent expression of the gene(s).

Stem cells of the invention can be genetically modified (e.g., by homologous recombination) to have a heterozygous knock-out of the Id1 gene, and a homozygous knockout of the Id3 gene. As described in co-owned and co-pending PCT Application No. PCT/USU3/01827 (Stem Cell-Derived Endothelial Cells Modified to Disrupt Tumor Angiogenesis), filed Jan. 22, 2003, these stem cells can be induced to differentiate into Id1+/−, Id3−/− endothelial cell precursor cells that are useful for the treatment of cancer because they give rise to endothelial cells that disrupt and inhibit tumor angiogenesis.

Stem cells of the invention can also be genetically modified to provide a therapeutic gene product that the patient requires, e.g., due to an inborn error of metabolism. Many genetic diseases are known to result from an inability of a patient's cells to produce a specific gene product. The present invention making genetically altered stem cells that can be used to produce cells with homozygous MHC alleles for transplantation that are genetically modified to synthesize enhanced amounts of a gene product required by the transplant recipient. For example, hematopoietic stem cells that are genetically altered to produce and secrete adenosine deaminase can be prepared for transplant to a patient suffering from adenosine deaminase deficiency. The methods of the present invention permit production of such cells without the use of recombinant retrovirus, which can insert at a site in the genomic DNA that disrupts normal growth control and causes neoplastic transformation.

Stem cells of the invention can also be genetically modified by introduction of a gene that causes the cell to die. The gene can be put under control of in inducible promoter. If for any reason the transplanted cells react in a in a way that can harm the recipient, expression of the suicide genes can be induced to kill the transplanted cells. Use of inducible suicide genes in this manner is known in the art. Suitable suicide genes include genes encoding HSV thymidine kinase and cytodine deaminase, with which cell death is induced by gancyclovir and 5-fluorocytosine, respectively.

The cells may be modified to knockout one or more histocompatibility antigen alletes, e.g., MHC alleles such that only one set remains. This leads to an underexpression of the MHC genes, but a phenotype effective in reducing the complexity of the MHC serotype and effective in producing cells capable of otherwise functioning and useful in the treatment of disease. Alternatively, homozygosity can be engineered into the cell lines by the targeted introduction of the appropriate alleles to the nonhomologous set, to result in homozygosity. In addition, the chromosome carrying the MHC genes can be removed from cells by laser ablation and a chromosome carrying the identical chromosome as remains in the cell can be added by microsome-mediated chromosome transfer, or by other techniques known in the art.

The present invention is by no means limited to the foregoing examples of genetic alterations. Persons skilled in the art will be able to identify numerous other ways by which stem cells produced according to the present invention can be genetically modified to enhance their utility.

Preparing Totipotent and/or Pluripotent Stem Cells:

Stem cells are present in the earliest stages of embryo formation. Embryonic stem cells (ES cells) are undifferentiated stem cells that are derived from the inner cell mass (ICM) of a blastocyst embryo. Totipotent and/or nearly totipotent ES cell lines can be derived from human blastocysts using known methods comprising removing cells of the inner cell mass of an early blastocyst by microsurgery or immuno-surgery and culturing the cells in vitro (e.g., see U.S. Pat. No. 6,235,970, the contents of which are incorporated herein by reference in their entirety). For example, such methods are described in co-owned and co-pending PC7 application, PCT/US02/37899 (Methods for Making and Using Reprogrammed Human Somatic Cell Nuclei and Autologous and Isogenic Stem Cells) filed Nov. 26, 2002, using blastocysts produced both by nuclear transfer and by parthenogenesis, the disclosure of which are incorporated herein by reference in its entirety. Thomson et al. also describes methods by which ES cell lines can be derived from primate/human blastocysts (*Science*, 1988, 282:1145-1147; and *Proc. Natl. Acad. Sci., USA*, 1995, 92:7544-7848), which are incorporated by reference herein in their entirety. A detailed method for preparing human ES cells is also described in Thomson's U.S. Pat. No. 6,200,806, "Primate Embryonic Cells," issued Mar. 13, 2001, the disclosure of which is incorporated herein by reference in its entirety. As described therein, a human ES cell line can be derived from cells of a blastocyst by a method comprising:

a. isolating a human blastocyst;

b. isolating cells from the inner cell mass of the blastocyst;

c. plating the inner cell mass cells on embryonic fibroblasts so that inner-cell mass-derived cell masses are formed;

d. dissociating the mass into dissociated cells;

e. replating the dissociated cells on embryonic feeder cells;

f. selecting colonies with compact morphologies and cells with high nucleus to cytoplasm ratios and prominent nucleoli; and g. culturing the selected cells to generate a pluripotent human embryonic stem cell line.

Methods for growing human ES cells and maintaining them in an undifferentiated state without culturing them on a layer of feeder cells have also been described (Xu et al., Nature Biotechnology, 2001, 19:971-4, the contents of which are incorporated herein by reference in their entirety). Feeder-free culture of stem cells can reduce the risk of contamination of the cells by pathogens that may reside in the feeder cells.

Generating Differentiated Cells:

Stem cells are widely regarded as an abundant source of pluripotent cellular material that can be directed to differentiate into cells and tissues that are suitable for transplantation into patients in need of such cell and tissue transplants. ES cells appear to have unlimited proliferative potential and are capable of differentiating into all of the specialized cell types of a mammal, including the three embryonic germ layers (endoderm, mesoderm, and ectoderm), and all somatic cell lineages and the germ line. Using known methods, totipotent or nearly totipotent ES cells can be cultured under conditions in which they differentiate into pluripotent or multipotent stem cells such as hematopoietic or neuronal stem cells. Alternatively, totipotent ES cells can be cultured under conditions in which they differentiate into a terminally differentiated cell type such as a cardiac muscle cell. Totipotent and/or pluripotent stem cells homozygous for MHC alleles produced by the methods of the present invention can be cultured using methods and conditions known in the art to generate cell lineages that differentiate into many, if not all, of the cell types of the body, for transplant into human patients in need of such transplants. Such stem cells having one or more homozygous MHC alleles can differentiate into cells selected from the group consisting of immune cells, neurons, skeletal myoblasts, smooth muscle cells, cardiac muscle cells, skin cells, pancreatic islet cells, hematopoietic cells, kidney cells, and hepatocytes. For example, methods have been described by which totipotent or nearly totipotent ES cells are induced to differentiate in vitro into cardiomyocytes (Paquin et al., Proc. Nat. Acad. Sci. (2002) 99:95509555), hematopoietic cells (Weiss et al., Hematol. Oncol. Clin. N. Amer. (1997) 11(6):1185-98; also U.S. Pat. No. 6,280,718), insulin-secreting beta cells (Assady et al., Diabetes (2001) 50(8):1691-1697), and neural progenitors capable of differentiating into astrocytes, oligodendrocytes, and mature neurons (Reubinoff et al., Nature Biotechnology (2001) 19:1134-1140; also U.S. Pat. No. 5,851,832).

Novel screening methods that make use of gene trapped cell lines and provide means for efficiently identifying combinations of biological, biochemical, and physical agents or conditions that induce stem cells to differentiate into cell types useful for transplant therapy, and for preparing and isolating specific differentiated cell types, are described in co-owned and co-pending U.S. application Ser. No. 10/227,282, filed Aug. 26, 2002, and in U.S. Provisional Application No. 60/418,333 ("Methods Using Gene Trapped Stem Cells for Marking Pathways of Stem Cell Differentiation And Making and Isolating Differentiated Cells"), filed Oct. 16, 2002, the contents of both of which are also incorporated herein by reference in their entirety.

In a useful embodiment of the present invention, a stem cell bank is produced that comprises hematopoietic stem cells homozygous for MHC antigens. A method for inducing the differentiation of pluripotent human embryonic stem cells into hematopoietic cells useful for transplant according to the present invention is described in U.S. Pat. No. 6,280,718, "Hematopoietic Differentiation of Human Pluripotent Embryonic Stem Cells," issued to Kaufman et al. on Aug. 28, 2001, the disclosure of which is incorporated herein by reference in its entirety. The method disclosed in the patent of Kaufman et al. comprises exposing a culture of pluripotent human embryonic stem cells to mammalian hematopoietic stromal cells to induce differentiation of at least some of the stem cells to form hematopoietic cells that form hematopoietic cell colony forming units when placed in methylcellulose culture.

Those skilled in the art will appreciate that, using currently available methodologies, the totipotent and pluripotent stem cells of the present invention can also be used to generate tissues formed of two or more different cell types homozygous for a MHC allele, for transplant to a person in need of such a tissue transplant.

The pluripotent and totipotent stem cells homozygous for MHC antigens that are generated according to the present invention, and the lines of differentiated cells obtained from these stem cells, are produced and isolated under Good Manufacturing Practices (GMP) conditions.

Providing Histocompatible Transplants to People Needing them:

The methods for generating stem cells and differentiated cells having homozygous MHC alleles described above provide effective solutions to many of the problems associated with obtaining cells for transplant that are histocompatible with a transplant recipient. However, de novo production of histocompatible cells and tissue for transplantation by in vitro fertilization, parthenogenesis, or nuclear-transfer-based methods for each patient in need of transplant is time-consuming. The time required to prepare "customized" cells or tissue for transplantation having the same HLA antigens as the transplant recipient can be problematic when the health of the would-be recipient is rapidly deteriorating for want of a transplant. Therefore, one or more of the above-described methods for generating stem cells and differentiated cells having homozygous MHC alleles are used to produce a stem cell bank comprising many different lines of stem cells, each having a different combination of homozygous MHC alleles present in the population. When a patient is found to be in need of a particular type of cell transplant, a line of stem cells from the stem cell bank having homozygous MHC alleles matching those of the patient can be taken "off the shelf" and cultured under conditions causing them to differentiate into the type(s) of cells needed. The differentiated cells are then isolated using known methods, and are provided to the patients physician for transplant.

Accordingly, the present invention includes the process of identifying the type of cells needed for transplant, and the blood type and HLA antigens of the transplant recipient, selecting stem cells from the stem cell bank that differentiate into the cell type needed and have homozygous HLA antigens that match those of the transplant recipient; culturing the stem cells under conditions in which they differentiate into the cell type needed; isolating the differentiated cells needed for transplant; and providing these to the patient's physician for transplant into the patient.

The differentiated cells for transplant produced by these methods are homozygous for at least one HLA antigen present on cells of the transplant recipient. Histocompatibility of the cells for transplant and the recipient increases as a function of the number of homozygous HLA antigens of the cells for transplant that match HLA antigens of the recipient. The greater the number of homozygous HLA antigens of the cells for transplant that match HLA antigens of the recipient, the longer the graft is expected to survive without being rejected. The cells for transplant provided by the invention will therefore have one, two, three, four, five, six, or more homozygous HLA antigens that match HLA antigens of the recipient. For example, cells for transplant produced by the present invention can have homozygous HLA-A, HLA-B, and HLA-DR antigens that match HLA antigens of the recipient. Alternatively, the cells for transplant produced by the present invention can have homozygous HLA-A, HLA-B, HLA-C, HLA-DR, HLA-DQ, and HLA-DP antigens that match HLA antigens of the recipient. The ability to select stem cells "off the shelf" to produce cells for transplant having a relatively high number of homozygous HLA antigens that match those of a prospective transplant recipient depends on the size and complexity of the stem cells bank. A stem cell bank containing from 100,000 to 200,000 different stem cell lines, each having a different combination of homozygous HLA-A, HLA-B, and HLA-DR antigens, is required in order to be able to provide cells with homozygous HLA-A. HLA-B, and HLA-DR antigens that match the corresponding HLA antigens of a large percentage of people in a diverse population such as that of North America. Use of cells from individuals with blood type 0 can avoid rejection based on ABO blood type; but there would have to be two versions of each cell type in the stem cell bank in order to provide matches to the Rh(+) and Rh(−) blood types. Accordingly, a stem cell bank containing several hundred thousand stem cell lines can be expected to provide "off the shelf" stem cells that can be used to generate differentiated cells needed for transplant that have homozygous HLA-A, HLA-B, and HLA-DR antigens matching those of a person in need of such a transplant.

The stem cell bank of the present invention contains lines of totipotent, nearly totipotent, and/or pluripotent human stem cells, each having a specific combination of one or more homozygous HLA antigens. The lines of stem cells that can be used to generate cells or tissue suitable for transplant can be lines of totipotent or nearly totipotent human ES cells. The stem cell lines can also be pluripotent, partially differentiated stem cells such as myoblasts, hematopoietic stem cells, neuronal precursor cells, and endothelial cell precursor cells.

Therapeutic Cell Transplantation:

Using the methods of the present invention, a line of totipotent or pluripotent stem cells can be selected from a bank of such stem cells that are homozygous for one or more histocompatibility antigen alleles, in the case of human stem cells. MHC alleles that match an MHC allele of a patient in need of transplant. For example, the stem cells can have homozygous HLA-A, HLA-B, and HLA-DR alleles that match HLA-A, HLA-B, and HLA-DR alleles of the patient. The stem cells are cultured ex vivo under conditions in which they are induced to differentiate into partially or fully differentiated cell types that are suitable for transplant and have homozygous MHC alleles that match MHC alleles of the patient in need of the transplant.

The partially or fully differentiated cells needed for transplant are isolated from other cell types, e.g., using antibody-based separation methods such as cell sorting or immunomagnetic beads, and antibodies that are specific for one or more differentiation antigens on the surface of the cell type needed for transplant, as described in U.S. Provisional Application No. 60/418,333, filed Oct. 16, 2002, the disclosure of which is incorporated herein by reference in its entirety. The isolated partially or fully differentiated cells are then administered by transplantation to the patient using known methods. Methods for transplantation of epidermal cells, hematopoietic stem cells. Islet of Langerhans cells, chondrocytes, hepatocytes, myoblasts, neural cells, and endothelial cells are reviewed by Inverardi et al. (Transplantation Biology, Cellular and Molecular Aspects, Chapter 56, 1996, ed. by Tilney et al., Lippincott-Raven, Philadelphia, Pa. The method to be used to transplant or engraft cells to a patient is recognized as depending on the type of cells to be transplanted, and on the pathology of the patient.

Cells Homozygous for Recessive Disease-Causing Genes:

Recessive alleles responsible for genetically inherited diseases are endemic in the population. If cells of people carrying a recessive disease-causing gene are used to produce stem cells having homozygous HLA alleles from embryos generated by parthenogenesis, or with sperm and eggs of closely related individuals, there is a relatively high likelihood that some of the stem cell lines obtained also be homozygous for the recessive disease-causing gene. The stem cell lines produced by the methods of the present invention can therefore be screened to identify those which are homozygous for a recessive disease-causing gene. Such screening can be carried out using known methods. For example, DNA sequences of the cells can be amplified by the polymerase chain reaction (PCR) and analyzed by DNA sequencing, restriction enzyme cleavage, or by hybridization to an array of oligomers, e.g., on a microchip. Examples of recessive-disease causing genes to be screened for include, but are not limited to, of recessive genes causing the following conditions:

Adenosine deaminase deficiency
Albinism
Adenylosuccinate lyase deficiency
Alpha-1 antitrypsin deficiency
Cystic Fibrosis
Friedreich's ataxia
Gaucher's disease
hypercholesterolemia
Alzheimer's Disease
Autoimmune polyendocrinopathy candidiasis-ectodermal dystrophy
AID—deficiency of activation-induced cytidine deaminase
Ataxia-telangiectasia
CD3—epsilon deficiency (causes SCID)
CD3—gamma deficiency (causes SCID)
chronic granulomatous disease—deficiency of $p47^{phox}$
Phenylketonuria—Phenylalanine hydroxylase (PAH) deficiency
Tetrahydrobiopterin deficiencies:
GTP cyclohydrolase I (GTPCH) deficiency
6-Pyruvoyl-tetrahydropterin synthase (PTPS) deficiency
Dihydropteridine reductase (DHPR) deficiency
Pterin-4a-carbinolamine dehydratase (PCD) deficiency
Janus Kinase 3 (JAK3) deficiency (causes SCID)
Hereditary fructose intolerance
Porphyria (one of the six forms is caused by a recessive gene)
Sickle Cell Anemia
Tay Sachs syndrome
Thalassemia
Wilson's disease
Xeroderma pigmentosum
Zeta-chain-associated protein kinase deficiency (causes SCID)

The totipotent and/or pluripotent stem cell lines having a homozygous recessive disease-causing gene that are produced by the methods of the present invention are highly useful. They can be cultured under conditions in which they differentiate into cell types related to manifestation of the disease phenotype. Such cells having a homozygous recessive disease-causing gene are useful for basic research directed to studying the disease phenotype ex vivo. They can also be implanted into experimental animals (e.g., immunodeficient animals), for study of their metabolic activities in vivo. Persons skilled in the art would recognize that studies in which such cells are genetically modified can be useful for gaining understanding of the disease phenotype. Such cells having a homozygous recessive disease-causing gene can also be used in drug discovery; e.g., in screening for drugs or other therapies that will treat or cure the disease caused by the recessive gene.

In order to further illustrate the invention and its preferred embodiments, the following examples are provided. These examples are intended to be exemplary and in no way limitative of the scope of the present invention.

Example 1

Production of Parthogenic Primate Primordial Stem Cells (PPSC's)

Materials and Methods
1. Cynomolgus Monkey (*Macaca fascicularis*) were superovulated using a single injection of 1000 IU of pregnant mare's serum gonadrophin (PMSG) and 500 IU of human chorionic gonadoprophin (hCG) four days later.
2. Ovaries were retrieved by laparotomy and oocytes dissected from the follicles and placed in maturation media 36 to 48 hrs after (hCG). Maturation media consisted of medium-199 (Gibco BRL) with Earle's balanced salt solution supplemented with 20% fetal bovine serum, 10 IU/ml of PMSG, 10 Mimi of hCG, 0.05 mg/ml of penicillin G and 0.075 mg/ml of streptomycin sulfate (Hong, 1999).
3. Oocyte activation
After 40 hrs in maturation, metaphase II eggs were placed in 10 micromoles of lonomycin followed incubation in 200 mM 6-DMAP (dimethylaminopurine) for 3 to 4 hrs.
4. Embryo culture. Commercially available embryo culture media 'Cooks' was used (modified SOF). Embryos were cultured with a co-culture of mitotically inactivated mouse embryonic fibroblasts as feeder layer.
5. Isolation of inner cell mass
  a) Upon development to blastocyst, embryos were placed in a buffered solution of 0.3% pronase for 2 minutes to digest zone pellucida
  b) Blastocyts were then rinsed in buffered solution and moved to solution of 01 culture media and polyclonal antibodies (antihuman whole serum) 1:3 dilution for 30 minutes.
  c) Embryos were rinsed 5 times in a buffered solution.
  d) Embryos were moved into a solution of G1 culture media and guinea pig complement 1:3 dilution for 30 minutes.
  e) Remaining of the embryos (dead trophoblast cells and ICM) were rinsed 5 times in buffered solution the Inner Cell Mass (ICM) was isolated and placed on top of a mouse embryonic fibroblast feeder layer for isolation and growth of Primordial Stem Cells (PSC's).

Results

Figure 2:
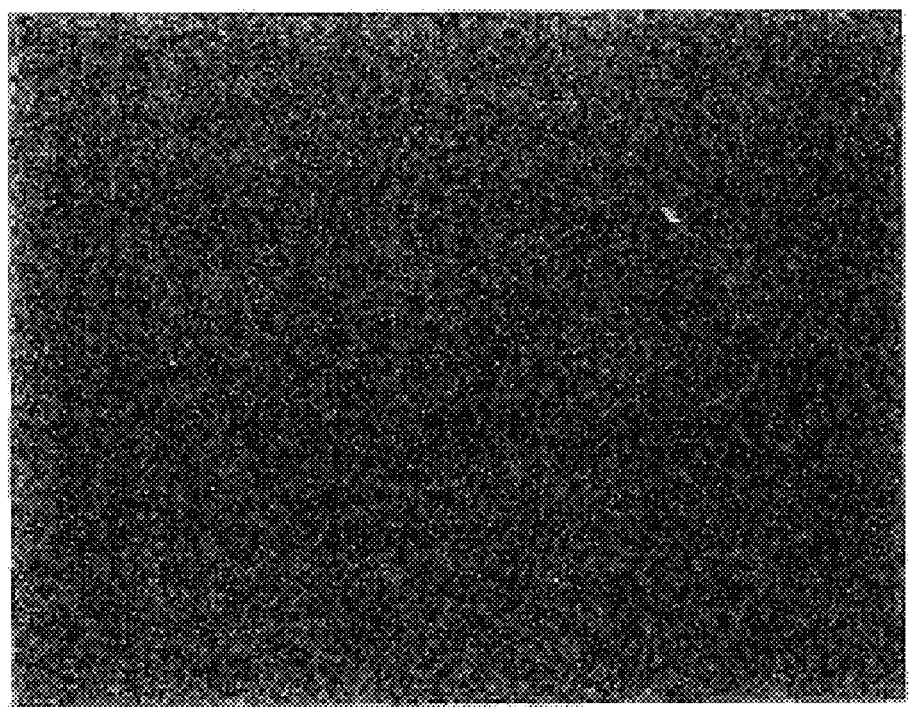
FIG. 2 shows an ES-like cell line (Cyno 1) derived from a cynomolgus parthenogenetic blastocyst.
Figure 3:
FIGS. 3 and 4 show the Cyno 1 cell line before and after immunosurgery.
Figure 4:
Figure 5:
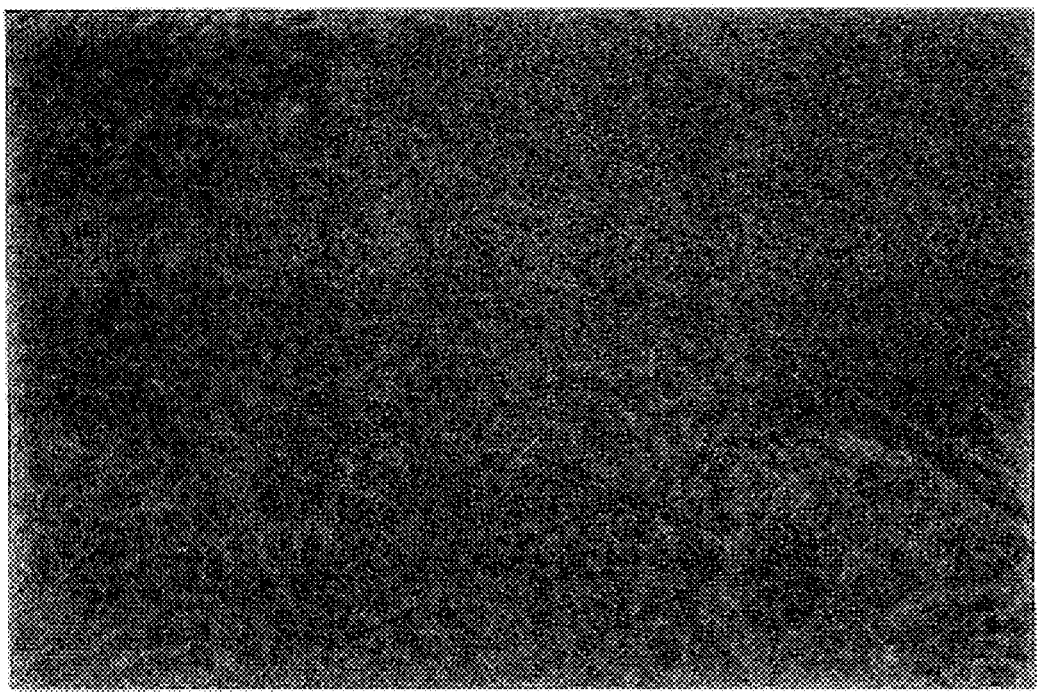
FIG. 5 shows the Cyno 1 cell line 5 days after plating.

We have obtained 450 eggs total, after maturation, 224 were still at germinal vesicle stage (GV=no maturation), 79 were dead, 56 were at metaphase one (MI) and 91 at metaphase two (MI1).
We have parthenogenically activated all of them. As expected, there was no cleavage on the GV group, 32% cleavage on the MI and 57% on the MII. When put in culture, 7 embryos developed to the blastocyst stage (See FIG. 1).
After attempting to establish ES-like culture cells, four Inner cell masses attached nicely one differentiated immediately, and out of the three remaining, one cell line was obtained. This cell line is called Cyno 1 (FIG. 2). This cell line before and after immunosurgery is shown in FIGS. 3 and 4. FIG. 5 shows the Cyno 1 Cell line five days after plating.

Figure 6:
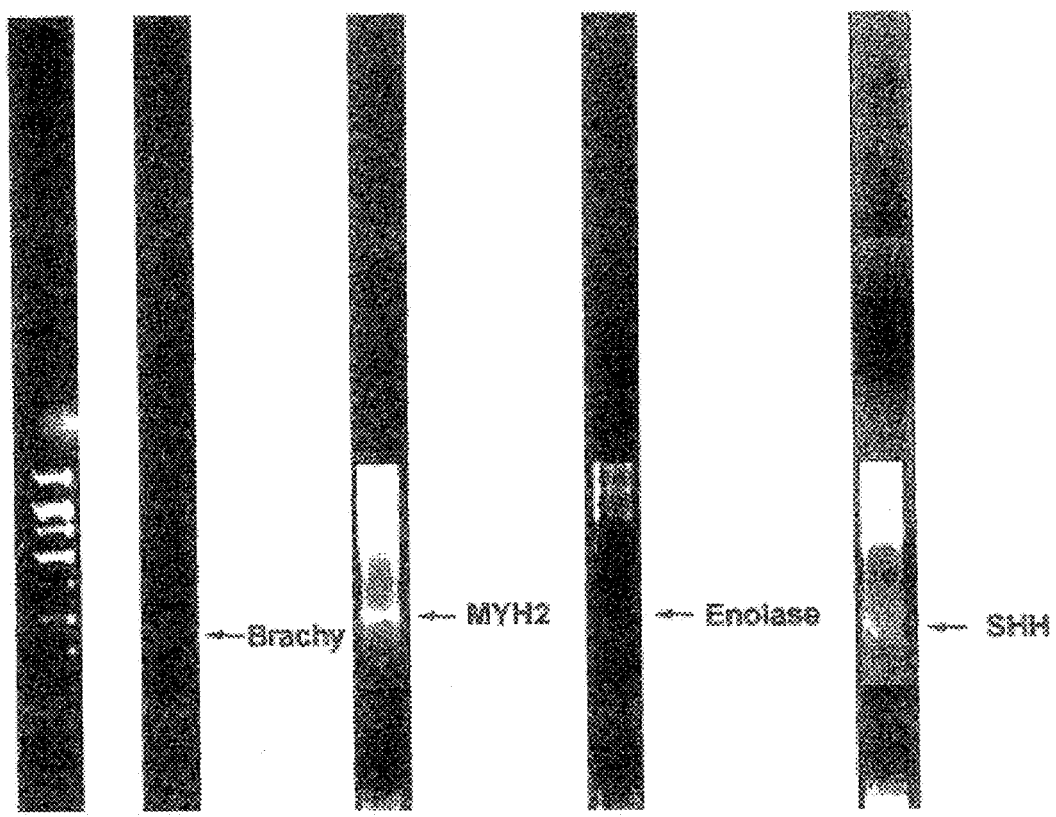
FIG. 6 shows the Cyno 1 cell line growing on top of a feeder layer.

FIG. 6 shows the Cyno 1 cell line growing on top of a mouse fibroblast feeder layer. These cells show typical morphology of pluripotent-embryonic-cells such as small nuclear cytoplasmic ration and the presence of cytoplasmic granules.

These cells were maintained in an undifferentiated state for a period of months. This is evidenced by screening of such cells after prolonged culturing for the expression of a cell marker characteristic of undifferentiated cells, Alkaline Phosphatase. As expected, cells were positive on passage 3 and on passage 5.

The fact that these cells maintain their pluripotency is also shown by their spontaneous differentiation into many differentiated cell types after being placed in tissue culture in the absence of a feeder layer. In the days following, the cells were observed to differentiate into cuboidal epithelium, fibroblasts, beating myocardial cells and other cells. Two colonies of beating myocardial cells were observed in one well of a 4-well tissue culture plate.

To determine whether differentiated cells of various somatic cell lineages were observed from the differentiating PPSC's, we extracted mRNA from differentiated cell cultures, performed RT-PCR, using human sequence primers specific for various differentiated cell types. As shown in FIG. 6, transcripts of a predicted size for the mesodermally-derived transcripts brachyury and skeletal muscle myosin heavy polypeptide 2 were observed. The transcript sonic hedgehog essential for endoderm development was observed. In addition, the neuron-specific ectoderm marker enolase was observed as well as keratin (not shown) as markers of ectodermally derived cells. These PCR products were not observed in the mouse feeder layer controls or in the absence of reverse transcriptase.

Figure 7:
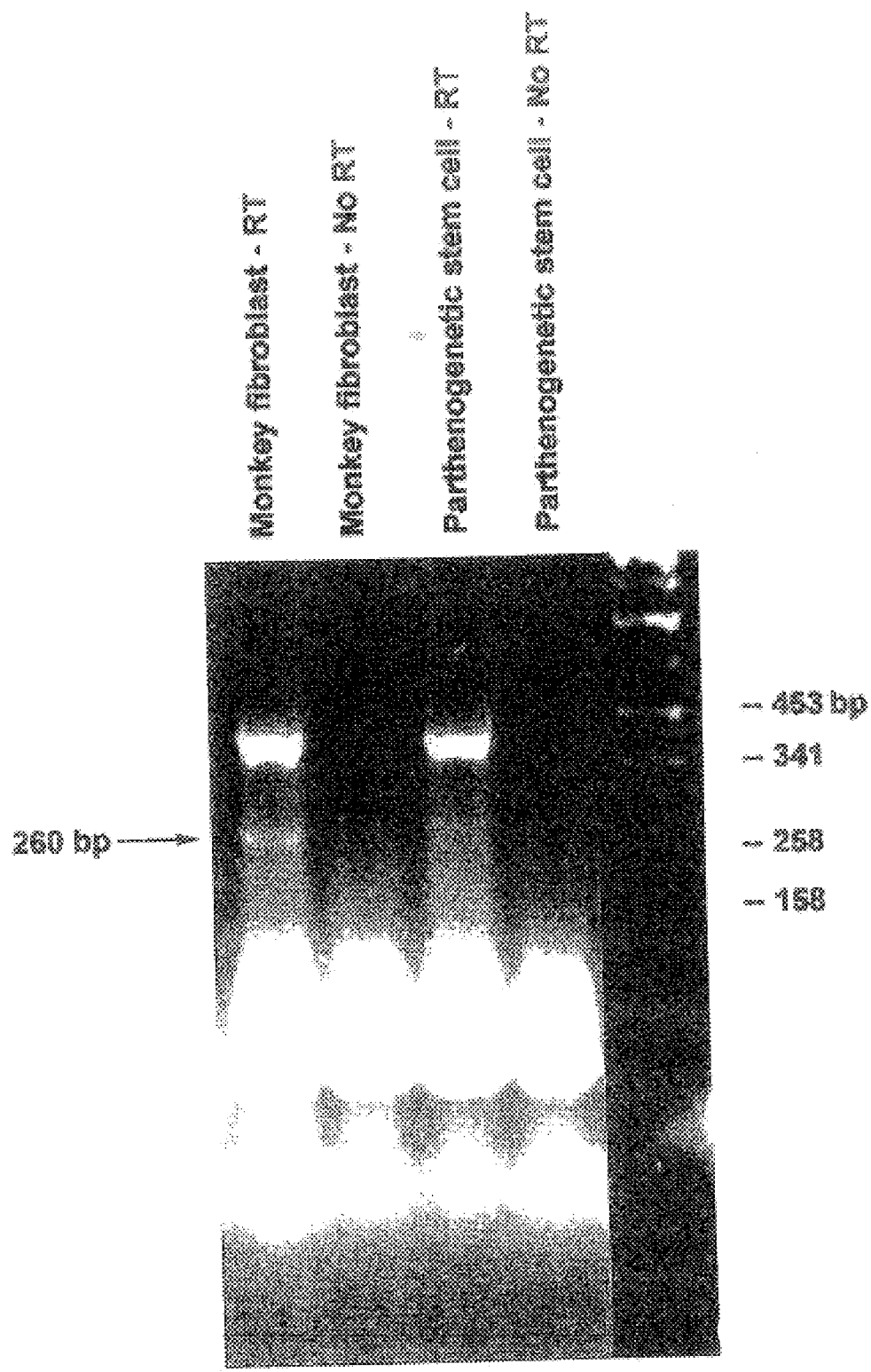
FIG. 7 shows the results of an RT-PCR showing that the Cyno-1 cell line is homozygous for the Snrpn gene (contains paternal allele).

To establish that the imprinting status of parthogenetic PPSC's different than that of di-parental PPSCs we looked at the expression of several imprinted genes. Genes that are mono-allelically expressed from the paternal allele, would not be expected to be expressed in parthogenetic cells, as these cells are derived exclusively from the maternal genome. The Snrpn gene is mono-allelically expressed from the paternal allele in mouse blastocyst inner cell mass [Szabo, P E and Mann, J R; Genes & Development 9:3097-3108 (1995)]. We looked at the expression of this gene in the parthogenetic *Macaca facicularis* PPSCs and found that the express was undetectable by RT-PCR, whereas under identical conditions, this gene is readily detected in fibroblast cell cultures from the same species. The Snrpn gene is expected to be expressed in diparental PPSCs, as these cells contain a paternal allele. In FIG. 7, the expected size RT-PCR product for the Snrpn gene is 260 bp.

Example 2

Stable Engraftment of Homozygous Fibroblasts in Histocompatible are Non-Histocompatible Cynomolgus Recipients Connective tissue fibroblasts are generated from the cyno-1 stem cell line described above which are labeled with green flourescent protein (GFP) gene. This cell line is homozygous as evidenced by the portion of a single allete of 225 basepairs using a primer set specific for DQB1u6011-17. These cells are propagated in vitro until several million cells are obtained.

Thereafter, approximately a million labeled connective fibroblasts are transplanted into histocompatible cynomolgus monkey recipients, and non-histocompatible cynomolgus controls. Each monkey is transplanted with a million labeled cells administered by injection in the upper arm at for different sites, in four equal parts.

The degree of engraftment of these engrafted labeled cells is assessed at three different times, at four weeks, six months and a year. Three of the four grafts are removed at three different times and the number of GFP labeled cells is determined in the histocompatible transplant recipients and controls. The number of GFP cells is compared for both groups.

Also, a histological examination is effected to look for any signs of lymphocyte infiltration and any signs of rejection.

Example 3

Production of Homozygous Stem Cell Lines from Rabbit Parthenogenically Activated Ooyctes Rabbit ES cells were similarly obtained from parthenogenetic embryos. Specifically, rabbit oocytes were obtained from superovulating rabbits and were actuated using ionomycin and DMAP. This resulted in blastocystes, the inner cell masses of which were transferred to fibroblast factor layer. This in turn resulted in the production of rabbit ES cell lines which stained positive for characteristic embryonic antigens and which gave rise to various differentiated cell types when removed from the front layer.

More specifically, true rabbit ES cell lines morphlogically looked like ES cells and differentiated into all three germ cell lineages. Among the cell types that observed from this cell line were myocordial, vascular endothalial, neuronal, and hemotopoiath cell lineages.

Example 4

Protection of Homozygous Stem Cell Lines from Human Parthenogenically Activated Oocytes Production of Autologous Cells by Parthenogenetic Activation of Oocytes Oocytes from three volunteers were used for parthenogenetic activation. The donors were induced to superovulate by 11 days of low dose (75 IU bid) gonadotropin injections prior to hCG injection. A total of 22 oocytes were obtained from the donors 34 hours after HCG stimulation, and were activated at 40-43 h after hCG stimulation. The oocytes ere activated on day 0, using the ionomycin/DMAP activation protocol described above. Twelve hours after activation, 20 oocytes (90%) developed one pronucleus and cleaved to the two-cell to four-cell stage on day 2. On day 5 of culture, evident blastocoele cavities were observed in six of the parthenotes (30% of the cleaved oocytes) though none of the embryos displayed a clearly discernible inner cell mass. The results of parthenogenetic activation of the human oocytes are summarized in Table 4.

TABLE 4

Parthenogenetic Activation of Human Oocytes

| Donor | No. of Oocytes | Pronucleus (%)[a] | Cleaved (%)[a] | Embryos with blastocoele Cavity (%)[b] |
|---|---|---|---|---|
| 1 | 5 | 4(80) | 4(80) | |
| 2 | 14 | 13(93) | 13(93) | 4(31) |
| 6 | 5 | 3 | 3(100) | 2(67) |
| Total | 22 | 20(90) | 20(90) | 6(30) |

[a]As a percentage of activated oocytes.
[b]As percentage of cleaved oocytes.

Figure 8:
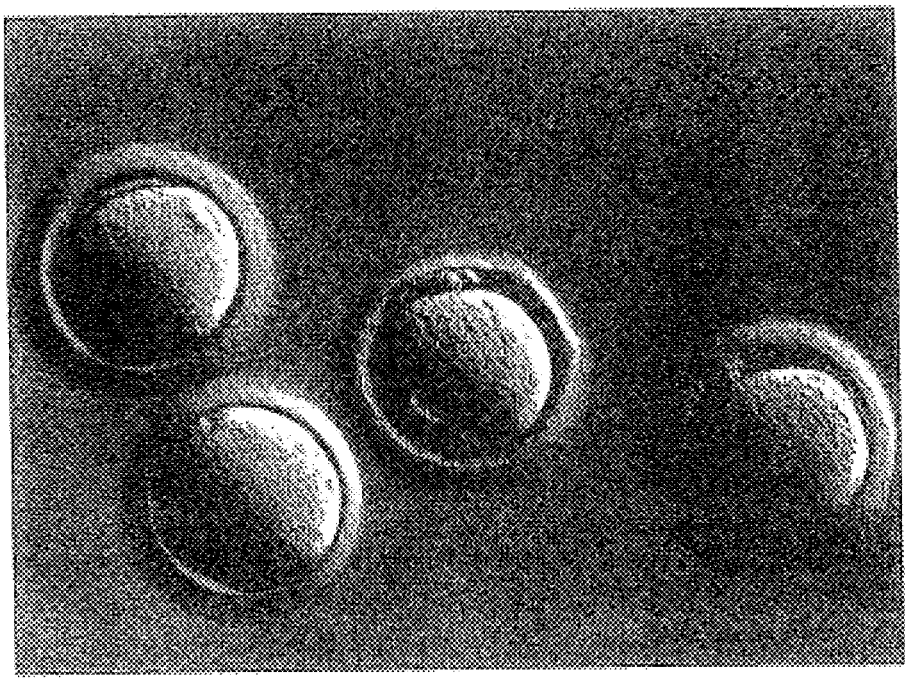
FIG. 8 shows metaphase II oocytes at retrieval.
Figure 9:
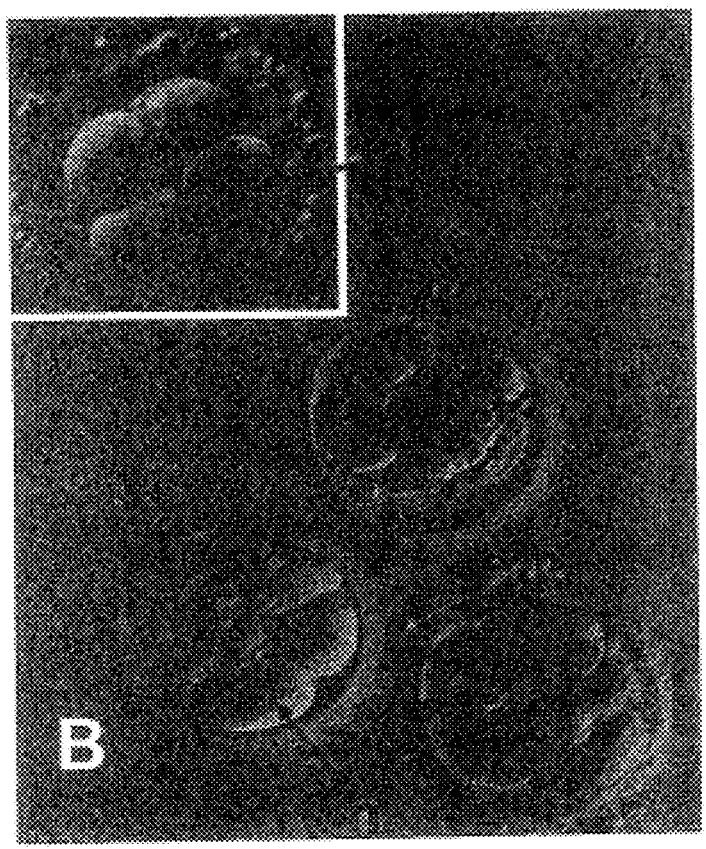
FIG. 9 shows 4 and 6 cell embryo 48 hours after parthenogenetic activation.
Figure 10:
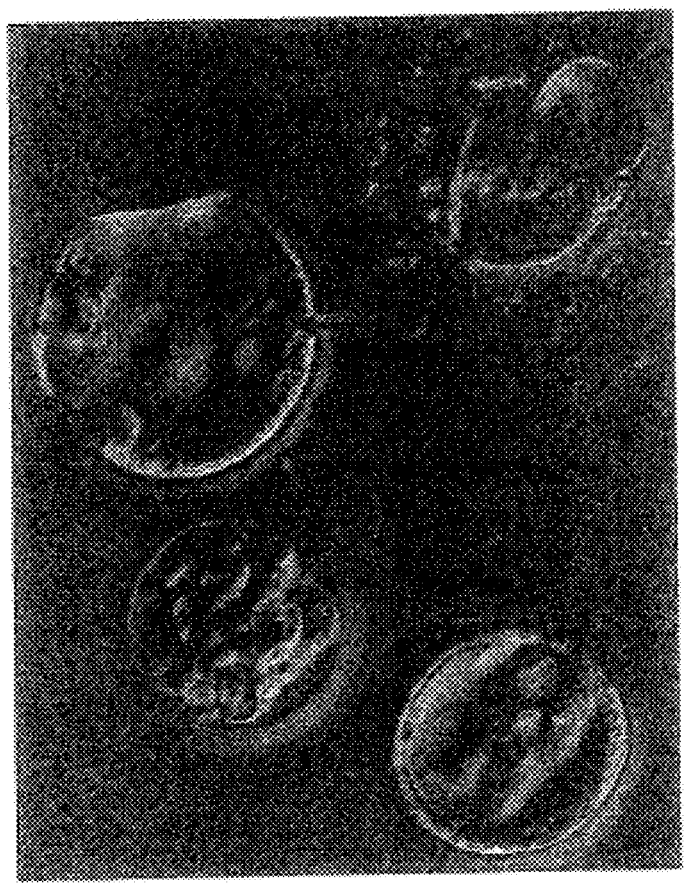
FIG. 10 shows blastocoele cavities in human parthenogenetic activation 48 hours after activation.

FIG. 8 shows MI I oocytes at the time of retrieval. FIG. 9 shows four- to six-cell embryos 48 h after activation. Distinguishable single-nucleated blastomeres (labeled "n" in FIG. 6) were consistently observed. FIG. 10 shows embryos with blastocoele cavities (arrows) that were detected on day 6 and maintained in culture until day 7. The scale bars for FIGS. 6-8=100

Figure 11:
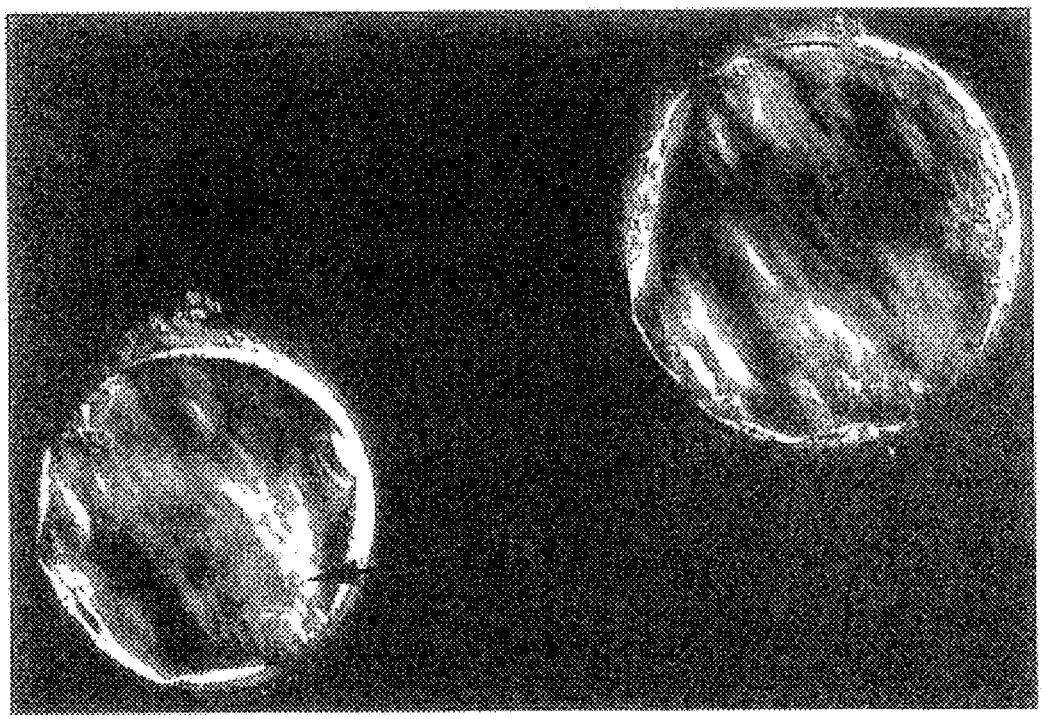
FIG. 11 shows human parthenogenetic embryo having an inner cell mass.
Figure 12:
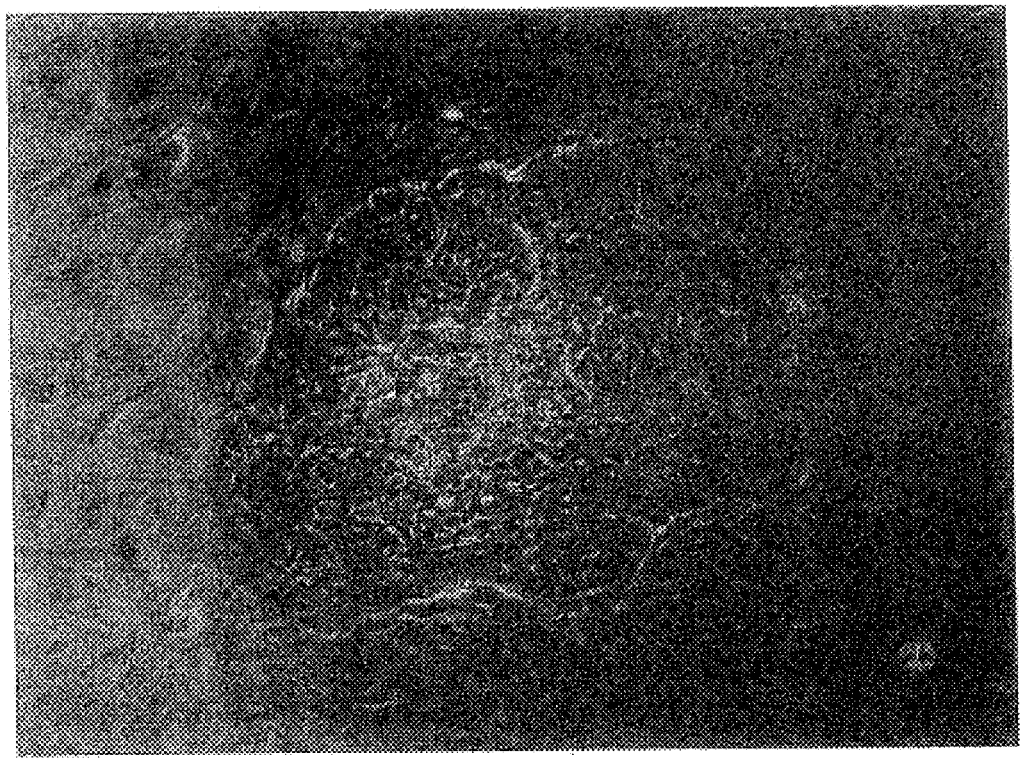
FIG. 12 shows human ES-like cells derived from cultured ICM cells.

In a study similar to the one described above, human oocytes were activated using the ionomycin/DIVIAP activation protocol and were cultured in vitro. One of the activated embryos developed a pronucleus, cleaved, formed a blastocoele cavity, and then developed into a blastocyst having an inner cell mass, shown in FIG. 11. The inner cell mass was isolated and plated on mouse feeder layers as described (Cibelli, J. B., et al. 2002. Parthenogenetic stem calls in non-human primates. Science 295: 819). The cultured ICIM cells increased in number over the first week, and cells indistinguishable from human embryonic stem cells were observed. These grew in close association as a colony with a distinct boundary, as shown in FIG. 12; they had a high nuclear-to-cytoplasmic ratio, prominent nucleoli, and were observed to differentiate in vitro into multiple differentiated cell types.

Example 5

Production of Homozygous Stem Cell Lines from Mouse Parthenogenically Activated Oocytes Using substantially the same methods described in the present application, another research group, Lin et al., Stem Cells 21:152-161 (2003) incorporated by reference in its entirety, generated stem cell lines from unfertilized mouse metaphase II oocytes. These oocytes were activated by 5 minute exposure to 5 mm calcium ionophore (ionomycin) followed by a 3 hour exposure to 6-methyldiaminopurine (DMAP). Those stem cell lines were characterized as stem cell lines based on their expression of characteristic embryonic antigens (SSEAs, OCT-4, alkaline phosphatase and telomerase) and their pluripotency (give rise to ectodermal, endodermal and mesodermal cell types).

Specifically, activated, unfertilized oocytes from F1 hybrid mice (H-2-B/DO were used to establish those stem cell lines homozygous for H-2-B and H-2-D respectively. The stem cell lines appeared karyotypically normal. When cultured in vitro in the pressures of specific growth factors, these cell lines gave rise to ectodermal, mesodermal, and endodermal cell types. Histological examination of cultures revealed cells having the morphology of neuronal cells and hemotopviette lineages (lymphocytes, monocytes and erythrocytes).

Further, when these cell lines were implanted in the kidney of syngenetic F1 mice they similarly resulted in teratomas that comprised cells of all three germ layers. The teratomas when histologically examined showed evidence of hair follicles, thyroid glands, lung epithelium and connective tissue.

CONCLUSIONS

The results in the foregoing examples provides proof of principle, namely that homozygous stem cell lines may be generated from embryos, e.g. parthenogenically activated embryos, and used to produce differentiated cell types for cell therapy. More specifically, the present instruction provides methods for making libraries or banks of stem cell lines that are homozygous for specific MHC alleles. Thereby, a bank of cells is available which can be used to produce differentiated cells which are histocompatible for a wide range of transplant recipients. This is feasible with a relatively few number of stem cell lines given that certain HLA haplotyes are expressed with relatively high frequency in the human population.

These differentiated cells should be well tolerated and be stably engrafted given their antigenic expression relative to the transplant recipient. Also, in the case of stem cell lines derived from parthenogenically activated oocytes, these cells eliminate certain ethical issues with therapeutic cloning, namely a viable embryo (capable of giving rise to an offspring) is never obtained or destroyed. These cells are useful for treating any condition wherein cell or tissue transplantation is therapeutically desirable, e.g. immune deficiencies, age-related deficiencies, cancer, autoimmune disorder, organ deficiencies, disease, or injury, burn, malignancy, cell proliferation disorders, hemotopoietic disorders, e.g. blood malignancy such as non-Hodgkins lymphoma, leukemia, inflammatory disorders, connective tissue disorder, dermatological disorder, ischemia, stroke, neurological disorders and the like. The present cell banks on particularly well suited for treating acute disease, particularly when there is not sufficient time to do therapeutic cloning. For example, those cells are useful in obtaining differentiated cells for treatment of conditions where the patient is near death, e.g., sepsis, stroke and other conditions where cell therapy is urgently needed. Also, the invention provides means for having cells on hand that express desired therapeutic polypeptides which are histocompatible.

I claim:

1. A library comprising a plurality of isolated, genetically modified human embryonic stem cell lines produced by the method comprising:
   (a) genetically modifying a checkpoint arrested, senescent or near senescent human donor cell to be homozygous for at least one MHC allele by the removal of one or more sets of MHC alleles by knockout or RNA interference or the addition of another homozygous set of MHC alleles;
   (b) isolating the nucleus from the genetically modified donor cell;
   (c) inserting the nucleus into an enucleated human oocyte to produce a nuclear transfer embryo;
   (d) activating said nuclear transfer embryo and culture the embryo until it forms a blastocyst comprising a discernable inner cell mass; and
   (e) isolating cells from the inner cell mass to produce an embryonic stem cell line
wherein each of said plurality of stem cell lines is homozygous for a different set of MHC alleles relative to the remaining members of the plurality of stem cell lines, wherein the stem cells have EPC-1 and telomerase activity greater than EPC-1 and telomerase activity in age-matched control cells of the same type that are not generated by nuclear transfer techniques.

2. The library of claim 1 which is comprised of at least five different stem cell lines, each member homozygous for a different combination of histocompatibility or MHC antigen alleles.

3. The library of claim 1 which is comprised of at least ten different stem lines, each member homozygous for a different combination of histocompatibility or MHC antigen alleles.

4. The library of claim 1 which is comprised of at least about 100 to 1000 different stem cell lines, each homozygous for a different combination of histocompatibility or MHC antigen alleles.

5. The library of claim 1 wherein all of the stem cell lines are O-negative.

6. The library of claim 1 wherein the library includes human stem cells that are homozygous for one or more of the following MHC alleles: HLA-A1, HLA-A2, HLA-A3, HLA-A24, HLA-A11, HLA-A28, HLA-A29, HLA-A32, HLA-B15, HLA-B5, HLA-B7, HLA-B8, HLA-B12, HLA-B14, HLA-B18, HLA-B35, and HLA-B40.

7. The library of claim 6 wherein all of said human stem cell lines are O-negative.

8. The library of claim 1 which includes stem cell lines which are homozygous for at least one of the following HLA-A, HLA-B and HLA-DR haplotype combinations: 1, 7, 2; 1, 8, 3; 2, 14, 1; 2, 35, 4; 2, 35, 8; 2, 44, 4; 3, 7, 2; 3, 7, 4; 3, 7, 8; 3, 35, 3.7, 8; 3, 35, 1; 31, 51, 4; and 32, 14, 7.

9. The library of claim 8 which contains cell lines homozygous for all of said HLA-A, HLA-B and HLA-DR haplotype combinations.

10. The library of claim 8 which is O-negative.

11. The library of claim 9 which is O-negative.

12. The library of claim 1, which contains a stem cell line homozygous for an MHC, allele selected from HLA-A, HLA-8, HLA-C, HLA-DR, HLA-DQ, and HLA-DP, wherein the cells are of the O-negative blood group.

13. The library of claim 1, which contains a stem cell line homozygous for the MHC alleles encoding HLA-A, HLA-B, and HLA-DR.

14. The library of claim 1, which contains a stem cell line homozygous for the MHC alleles encoding HLA-A, HLA-B, and HLA-DR, wherein the cells are of the o-negative blood group.

15. The library of claim 1, which contains lines of diploid stem cells in which all of the MHC alleles are homozygous.

16. The library of claim 1, wherein the stem cells have telomeres that are on average at least as long as the telomeres of age-matched control cells of the same type that are not generated by nuclear transfer techniques.

17. The library of claim 16, wherein the proliferative life-span of the stem cells is at least as long as the proliferative life-span of age-matched control cells of the same type that are not generated by nuclear transfer techniques.

18. The library of claim 16, wherein the proliferative life-age-matched control cells of the same type that are not generated by nuclear transfer techniques.

* * * * *